United States Patent
Hamman et al.

(10) Patent No.: US 9,920,313 B2
(45) Date of Patent: Mar. 20, 2018

(54) CELL WASHING DEVICE USING A WAVE

(71) Applicant: Biomet Biologics, LLC, Warsaw, IN (US)

(72) Inventors: Ned M. Hamman, Leesburg, IN (US); Michael D. Leach, Warsaw, IN (US); David Abeskaron, Warsaw, IN (US)

(73) Assignee: Biomet Biologics, LLC, Warsaw, IN (US)

( * ) Notice: Subject to any disclaimer, the term of this patent is extended or adjusted under 35 U.S.C. 154(b) by 673 days.

(21) Appl. No.: 14/519,317

(22) Filed: Oct. 21, 2014

(65) Prior Publication Data
US 2015/0111277 A1    Apr. 23, 2015

Related U.S. Application Data

(60) Provisional application No. 61/893,555, filed on Oct. 21, 2013, provisional application No. 61/979,695, (Continued)

(51) Int. Cl.
*C12N 13/00* (2006.01)
*A61K 35/18* (2015.01)
(Continued)

(52) U.S. Cl.
CPC .............. *C12N 13/00* (2013.01); *A61K 35/18* (2013.01); *A61L 33/0094* (2013.01);
(Continued)

(58) Field of Classification Search
CPC ............. G01N 15/1404; G01N 21/453; G01N 2015/142; G01N 21/00; G01N 1/4077;
(Continued)

(56) References Cited

U.S. PATENT DOCUMENTS

| 1,909,756 A | 5/1933 | Claypool |
| 4,710,162 A | 12/1987 | Johnson |

(Continued)

FOREIGN PATENT DOCUMENTS

| WO | WO-2012125470 A1 | 9/2012 |
| WO | WO-2012125470 A1 | 9/2012 |

(Continued)

OTHER PUBLICATIONS

International Search Report and Written Opinion dated Feb. 25, 2015 for PCT/US2014/061523 claiming benefit of U.S. Appl. No. 14/519,302, filed Oct. 21, 2014, U.S. Appl. No. 14/519,284, filed Oct. 21, 2014, U.S. Appl. No. 14/519,317, filed Oct. 21, 2014, claiming benefit of U.S. Appl. No. 62/011,992, filed Jun. 13, 2014, claiming priority of U.S. Appl. No. 61/979,695, filed Apr. 15, 2014, claiming priority of U.S. Appl. No. 61/893,555, filed Oct. 21, 2013.

(Continued)

*Primary Examiner* — Walter D. Griffin
*Assistant Examiner* — Cameron J Allen
(74) *Attorney, Agent, or Firm* — Schwegman Lundberg & Woessner, P.A.

(57) ABSTRACT

A system is disclosed for washing a selected component and removing the selected component from a wash material. The selected component may include red blood cells that are washed to remove a rejuvenating solution. The red blood cells may then be removed with various systems, such as a standing acoustic wave system from the wash solution. Pumps and flow restrictors that provide steady flow from pumps that generate pulsed flow are also disclosed.

29 Claims, 13 Drawing Sheets

Related U.S. Application Data filed on Apr. 15, 2014, provisional application No. 62/011,992, filed on Jun. 13, 2014.

(51) Int. Cl.

| | |
|---|---|
| *A61L 33/00* | (2006.01) |
| *B01D 21/28* | (2006.01) |
| *F04C 2/00* | (2006.01) |
| *A61M 1/02* | (2006.01) |
| *B01L 3/00* | (2006.01) |
| *G01N 15/14* | (2006.01) |
| *A61M 1/36* | (2006.01) |
| *A61K 35/12* | (2015.01) |
| *G01N 33/49* | (2006.01) |
| *G01N 15/10* | (2006.01) |
| *G01N 15/02* | (2006.01) |

(52) U.S. Cl.
CPC ........ *A61M 1/0209* (2013.01); *A61M 1/0281* (2013.01); *A61M 1/3678* (2014.02); *A61M 1/3692* (2014.02); *A61M 1/3693* (2013.01); *B01D 21/28* (2013.01); *B01D 21/283* (2013.01); *B01L 3/502761* (2013.01); *F04C 2/00* (2013.01); *G01N 15/1459* (2013.01); *A61K 2035/124* (2013.01); *B01L 2200/0652* (2013.01); *B01L 2400/0433* (2013.01); *G01N 33/4915* (2013.01); *G01N 2015/0288* (2013.01); *G01N 2015/1006* (2013.01); *G01N 2015/149* (2013.01)

(58) Field of Classification Search
CPC ... G01N 2015/0288; G01N 2001/4072; B01D 17/06; B01D 57/02; B01D 17/00; B01D 17/12; B03B 5/60; C12N 13/00
See application file for complete search history.

(56) References Cited

U.S. PATENT DOCUMENTS

| | | |
|---|---|---|
| 7,674,100 B2 | 3/2010 | Hayes-pankhurst et al. |
| 7,837,040 B2 | 11/2010 | Ward et al. |
| 7,846,382 B2 | 12/2010 | Strand |
| 9,103,842 B2 | 8/2015 | Gray et al. |
| 2003/0029809 A1 | 2/2003 | Mchale |
| 2009/0066936 A1 | 3/2009 | Huang et al. |
| 2010/0000910 A1 | 1/2010 | Gallup et al. |
| 2010/0139377 A1 | 6/2010 | Huang et al. |
| 2011/0134426 A1* | 6/2011 | Kaduchak .......... G01N 15/1404 356/337 |
| 2011/0136645 A1 | 6/2011 | Ellingboe et al. |
| 2012/0196314 A1 | 8/2012 | Nawaz et al. |
| 2013/0043170 A1* | 2/2013 | Rose .................... B01D 21/283 209/659 |
| 2013/0048565 A1 | 2/2013 | Fiering et al. |
| 2014/0033808 A1 | 2/2014 | Ding et al. |
| 2014/0065117 A1 | 3/2014 | Gray |
| 2014/0193381 A1* | 7/2014 | Warner ............... A61M 1/3692 424/93.7 |
| 2014/0212400 A1 | 7/2014 | Gray |
| 2015/0110763 A1 | 4/2015 | Leach |
| 2015/0111195 A1 | 4/2015 | Hamman et al. |

FOREIGN PATENT DOCUMENTS

| | | |
|---|---|---|
| WO | WO-2012135663 A2 | 10/2012 |
| WO | WO-2012135663 A2 | 10/2012 |
| WO | WO-2015061284 A1 | 4/2015 |

OTHER PUBLICATIONS

Invitation to Pay Additional Fees and Where Applicable Protest Fee mailed Jan. 7, 2015 for PCT/US2014/061523 claiming benefit of U.S. Appl. No. 14/519,302, filed Oct. 21, 2014, U.S. Appl. No. 14/519,284, filed Oct. 21, 2014, U.S. Appl. No. 14/519,317, filed Oct. 21, 2014, claiming benefit of U.S. Appl. No. 62/011,992, filed Jun. 13, 2014, claiming priority of U.S. Appl. No. 61/979,695, filed Apr. 15, 2014, claiming priority of U.S. Appl. No. 61/893,555, filed Oct. 21, 2013.
Petersson, F., Aberg, L., Sward-Nilsson, A.M. and Laurell, T. Free Flow Acoustophoresis: Microfluidic-Based Mode of Particle and Cell Separation. Analytical Chemistry, vol. 79, No. 14 (Jul. 15, 2007) pp. 5117-5123.
Petersson, F., Nilsson, A., Jonsson, H. and Laurell. Carrier Medium Exchange through Ultrasonic Particle Switching in Microfluidic Channels. Analytical chemistry, vol. 77, No. 5 (Mar. 1, 2005) pp. 1216-1221.
Shi, J., Mao, X., Ahmed, D., Colletti, A., and Huang, T. Focusing mircroparticles in a microfluidic channel with standing surface acoustic waves (SSAW). Lab Chip. vol. 8 (2008) pp. 221-223.
"European Application Serial No. 14793393.1, Office Action dated Jun. 9, 2016", 1 pg.
"European Application Serial No. 14793393.1, Response filed Dec. 12, 2016 to Communication pursuant to Rules 161(1) and 162 EPC dated Jun. 10, 2016", 18 pgs.
"International Application Serial No. PCT/US2014/061523, International Preliminary Report on Patentability dated May 6, 2016", 12 pgs.
"International Application Serial No. PCT/US2014/061523, International Search Report dated Feb. 25, 2015", 9 pgs.
"International Application Serial No. PCT/US2014/061523, Written Opinion dated Feb. 25, 2015", 10 pgs.
"U.S. Appl. No. 14/519,284, Non Final Office Action dated Aug. 16, 2017", 11 pgs.
"U.S. Appl. No. 14/519,302, Non Final Office Action dated Oct. 4, 2017", 11 pgs.
"U.S. Appl. No. 14/519,302, Response filed Sep. 7, 2017 to Restriction Requirement dated Aug. 25, 2017", 7 pgs.
"U.S. Appl. No. 14/519,302, Restriction Requirement dated Aug. 25, 2017", 6 pgs.
"U.S. Appl. No. 14/519,284, filed Nov. 9, 2017 to Non Final Office Action dated Aug. 16, 2017", 10 pgs.

* cited by examiner

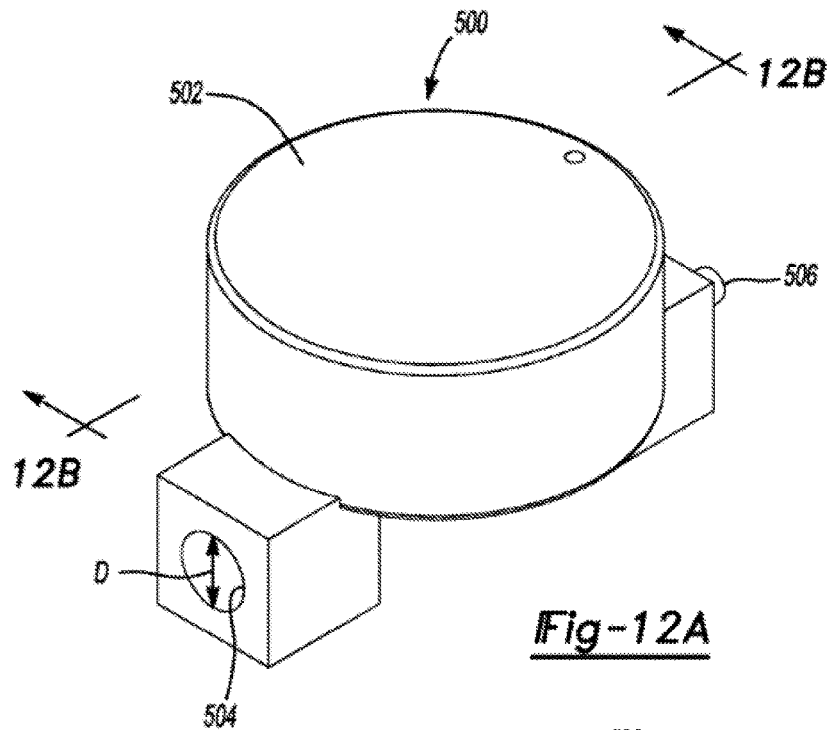
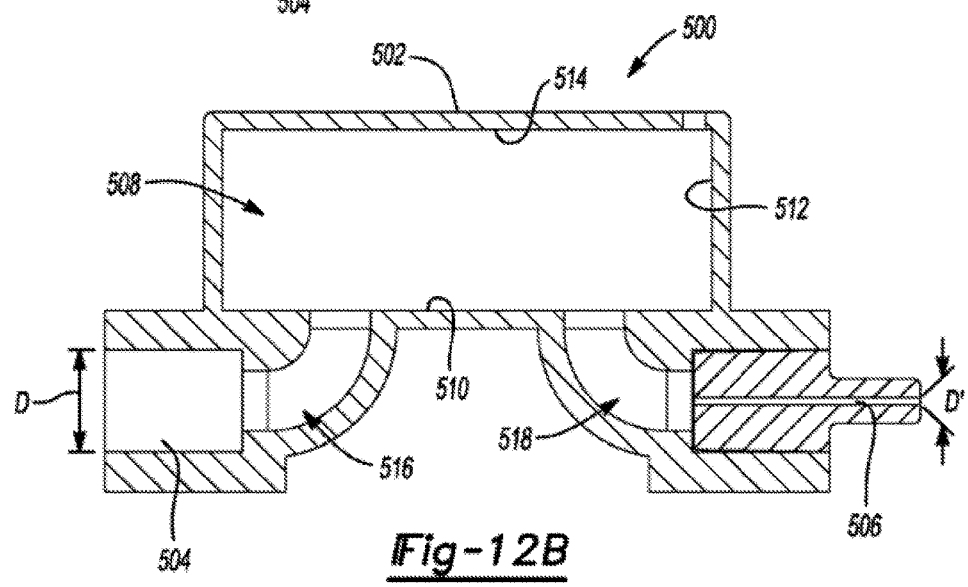

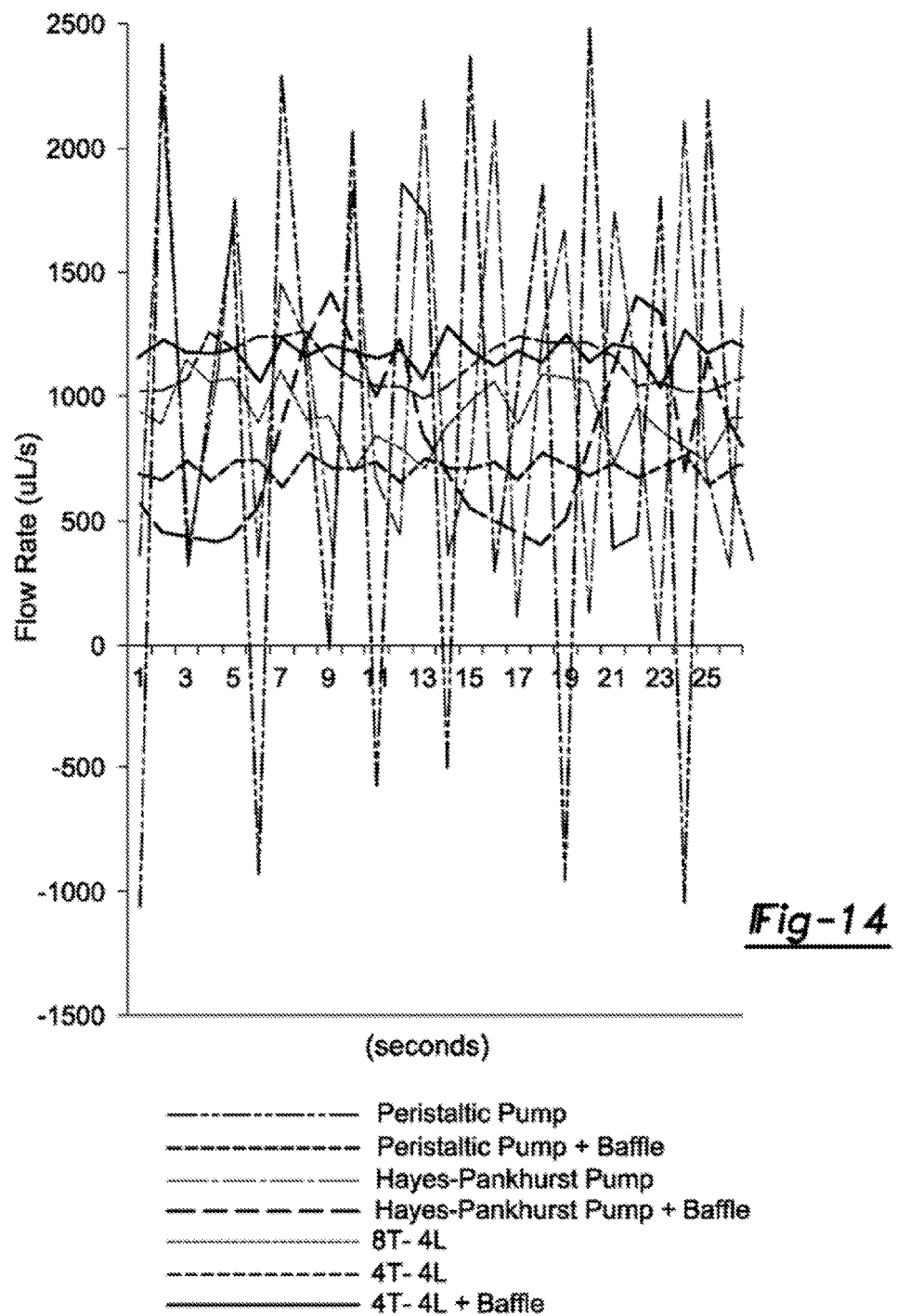

CELL WASHING DEVICE USING A WAVE

CROSS-REFERENCE TO RELATED APPLICATIONS

This application claims the benefit and priority of: (1.) U.S. Provisional Application No. 61/893,555 filed on Oct. 21, 2013; (2.) U.S. Provisional Application No. 61/979,695 filed on Apr. 15, 2014; and (3.) U.S. Provisional Application No. 62/011,992 filed on Jun. 13, 2014. The entire disclosure of the above applications are incorporated herein by reference.

FIELD

The subject disclosure relates to separating components from a mixture (including a suspension), and particularly to separating a selected component in a high concentration and purity using a wave.

BACKGROUND

This section provides background information related to the present disclosure which is not necessarily prior art.

A standing wave can also be referred to as a stationary wave. Generally, a standing or stationary wave can be formed from various mechanics, including interference between two waves. For example, two opposing waves can move towards one another in a medium and cause the formation of a standing wave. Alternatively, or in addition to the opposing waves, a medium can move in a direction opposite the wave to cause a standing wave. Generally, the standing wave, or wave pattern, includes a wave node (a point where the wave has zero amplitude) and a wave anti-node (where a wave has a maximum amplitude) relative to an axis.

Waves can be generated as surface waves, including surface acoustic waves. The surface acoustic waves can also be generated as standing surface acoustic waves. A surface wave may be a wave that is generated on or within a surface or substrate that may then interact with a material within a space and/or a channel formed on or in the substrate.

Pumps may be used to deliver the material to the substrate. However, many pumps, such as various rotary pumps, pump fluid in a pulsed flow. A pulsed flow would be disadvantageous when delivering a material into a standing wave because it can cause unwanted disruptions in the material between pulses. Therefore, a rotary pump that pumps fluid in a continuous flow is desirable for delivering a material into a substrate wherein the material interacts with a surface wave. Additionally, devices for generating a steady flow rate from a pulsed flow rate provided by a pump are also desired.

SUMMARY

This section provides a general summary of the disclosure, and is not a comprehensive disclosure of its full scope or all of its features.

According to various systems, acoustic waves can be generated, including surface acoustic waves (SAW) that are generated with acoustic wave generators. The acoustic wave generator can also be used to generate a SAW on a surface and/or in a substrate to generate a standing surface acoustic wave (SSAW) for various purposes. For example, a SAW or SSAW can be used to assist in separating and sorting a component of a multi-component mixture or solution, such as whole blood.

According to various embodiments, including those discussed further herein, a SAW can be used to separate a selected one or more components from a flow of a multi-component material, such as whole blood. It is further understood that a selected component can be separated from either a non-homogeneous material or a substantially pure material that has been mixed in a solute or mixed with a solute and/or wash. For example, a substantially pure red blood cell (RBC) sample can be washed with a wash material and a SAW can be used to separate and/or assist in a separation of the RBCs from the wash material. It is understood that the wash material can be provided for various purposes including removing undesired contaminants, such as dead cells, storage medium, rejuvenating material, and wash material, from a final collection of cells. A rejuvenating material may also be used for rejuvenating cells, such as maintaining or increasing an oxygen-carrying or exchange capacity of a RBC.

The present technology also provides a system for separation of a component from a wash material including a base unit and a disposable set. The base unit includes mounts and either a wave generator or electrical contacts and components selected from the group consisting of first and second pumps, first and second valves, first and second sensors, a plurality of clips and combinations thereof. The disposable set includes a separation chip coupled to a first pulse suppressor and a second pulse suppressor, a first conduit coupled to the first pulse suppressor at a first end of the first conduit, and a second conduit coupled to the second pulse suppressor at a first end of the second conduit, and a third and fourth conduit coupled to the separation chip at a first end of the third conduit and at a first end of the fourth conduit. The separation chip has a wave generator when the base unit comprises electrical contacts. The separation chip of the disposable set snaps into the mounts of the base unit. Separations can be performed without adjusting the disposable set when it is positioned on the base unit.

The present disclosure further provides a pump for delivering a multi-component material to a SAW. The pump comprises a housing having an inlet and an outlet, and a rotor. The rotor has a rotor body extending along a central longitudinal axis. The rotor body defines a sleeve at a first end, and a plurality of lobes that extend from the sleeve and spiral around the longitudinal axis to a second end of the housing. The lobes make from a ⅛ turn to about a ¾ turn above the central longitudinal axis. The rotor can have from 2 to 10 lobes. The pump is configured to pump a fluid at a continuous flow rate.

The present technology also provides for pulse suppressors and flow restrictors for providing steady and continuous flow rates from pumps that generate pulsed flow.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 12A is a schematic illustration of a pulse suppressor;

FIG. 12B is a cross-sectional perspective of the pulse suppressor taken along line 12B of FIG. 12A;

FIG. 14 is a graph that shows flow rates of various pumps over a course of time.

Corresponding reference numerals indicate corresponding parts throughout the several views of the drawings.

DETAILED DESCRIPTION

Example embodiments will now be described more fully with reference to the accompanying drawings.

SAW Separations

A surface acoustic wave (SAW) can be a wave or wave pattern selected to assist in separation of a component or material from a mixture or solution. For example, a SAW can be generated with a SAW generator to focus and/or separate a component of a mixture. SAW is known generally and it is known that one or more transducers, such as interdigitated transducers (IDTs), may form a SAW generator. Various SAW generators and focusing systems can include those disclosed in U.S. Patent Application Publication No. 2009/0066936 to Huang et al., published Mar. 12, 2009; U.S. Patent Application Publication No. 2010/0139377 to Huang et al., published Jun. 10, 2010; and U.S. Patent Application Publication No. 2012/0196314 to Nawaz et al., published Aug. 2, 2012; all the above applications are incorporated herein by reference in their entirety. As disclosed in U.S. Publication 2010/0139377 and illustrated in FIG. 8A, a pair of transducers 300 can be used to, for example, generate a selected number of pressure nodes within a channel to focus selected particles within the nodes. As discussed further herein, and illustrated in FIG. 2, at least one SAW generator can include a transducer that can generate a wave, including a SAW, to focus and/or separate a selected component in a flow path and or from a flow path. A generated wave, as is understood by one skilled in the art, may be any appropriate wave including an acoustic wave, liquid wave, etc. A standing SAW (SSAW) can be generated by positioning a two IDTs on one surface of a piezoelectric material. Any piezoelectric material known in the art can be used to generate a SAW. Non-limiting examples of piezoelectric materials include quartz, quartz crystal, ceramic, ceramic composites, berlinite ($AlPO_4$), lead titanate ($PbTiO_3$), barium titanate ($BaTiO_3$), lead zirconate titanate ($Pb[Zr_xTi_{1-x}]O_3$, $0 \leq x \leq 1$; "PZT"), potassium niobate ($KNbO_3$), lithium niobate ($LiNbO_3$), lithium tantalate ($LiTaO_3$), sodium tungstate ($Na_2WO_3$), $Ba_2NaNb_5O_5$, $Pb_2KNb_5O_{15}$, zinc oxide (ZnO), sodium potassium niobate (($K,Na$)$NbO_3$), bismuth ferrite ($BiFeO_3$), sodium niobate ($NaNbO_3$), bismuth titanate ($Bi4Ti_3O_{12}$, sodium bismuth titanate $Na_{0.5}Bi_{0.5}TiO_3$, and polymers, such as polyvinylidene fluoride (PVDF).

Figure 1:
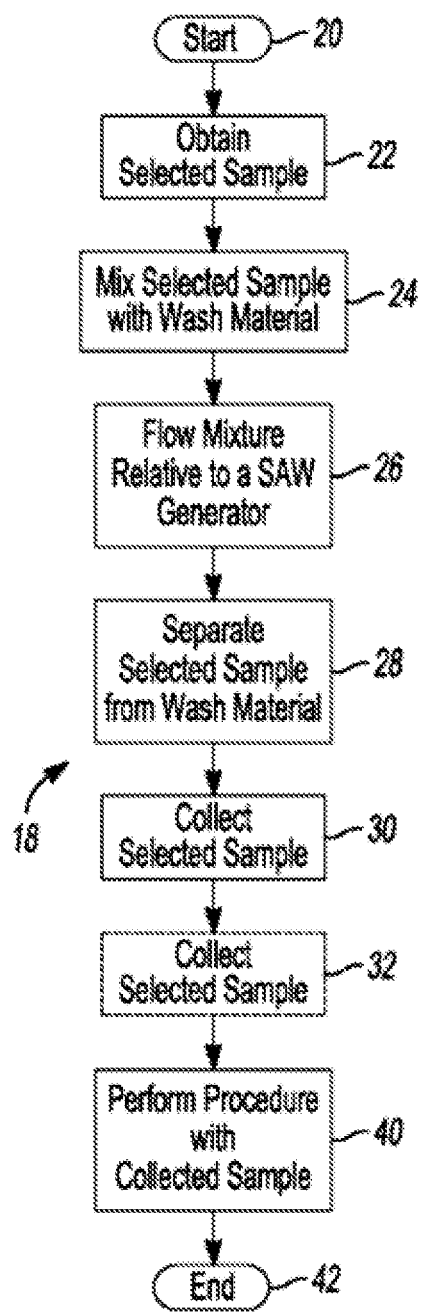
FIG. 1 is a flow chart illustrating a method of collecting a selected component.

With reference to FIG. 1, a flow chart illustrates a method or procedure 18 for washing and collecting a selected sample, according to various embodiments. Initially, the procedure 18 can start at block 20. In block 22, a selected sample can be obtained. The selected sample can include appropriate materials such as whole blood, separated blood, or other multiple component materials. Separated blood can include a blood sample that has a high concentration of Red Blood Cells (RBCs) and/or other blood cell components. A wash material can also be obtained and/or added to the obtained selected material from block 22. The selected sample can be mixed with the wash material in block 24. The wash material can also be obtained or selected before mixing with the RBC material.

Wash materials are generally known and can include sterile water, sterile saline, dextrose, and other wash liquids. According to various embodiments, the wash material may include sterile saline with 5% dextrose. The wash material may be suitable for infusion into a subject, such as a human subject. The selected sample, according to various embodiments, may include material that is desirable to be removed prior to use in a procedure, such as an infusion. Various materials to be removed may include various rejuvenating materials.

The rejuvenating material can assist in rejuvenating or recreating an oxygen carrying ability, such as an oxygen affinity, of RBCs. In one example a rejuvenating material can include Rejuvesol® rejuvenating solution for regeneration of RBCs and it can be used as a wash material. The Rejuvesol® rejuvenating solution is sold by Citra Labs, LLC, having a place of business in Warsaw, Ind., USA. Other appropriate rejuvenating materials include those disclosed in U.S. patent application Ser. Nos. 13/844,773; 13/756,116; and U.S. Patent Pub. No. 2014/0065117 to Gray, published Mar. 6, 2014, all of which are incorporated herein by reference. It is understood, however, that any appropriate wash material can be used to wash a selected sample.

Moreover, a selected sample need not include or solely include RBCs. The examples discussed herein, however, refer to RBCs that can be washed with a material to remove selected materials, such as a rejuvenating solution, including Rejuvesol® rejuvenating solution, for selected purposes. Other materials can be mixed with a wash material as well, including white blood cells, selected proteins, enzymes, selected cell phenotypes, etc. It is also understood, that the process may be understood to be removing or concentrating the RBCs from the wash material after a wash mixing.

The mixing can further occur in a selected mixing environment, such as in an agitation mixture, a magnetic bar mixer, a blending mixer, or other appropriate mixing apparatus. In some embodiments, mixing occurs as the wash material comes in contact with the obtained selected material in, for example, a flow conduit. Further, the mixing can occur at selected environmental conditions, including temperature, pressure, humidity, and the like. For example, the mixing of the wash material and RBCs can occur at about 30° C. to about 36° C. for a selected period of time, including about two minutes to about ten minutes, and further including about five minutes. The mixture can then be flowed relative to a separating system, which may include a SAW generator in block 26. In various embodiments, the SAW generator is an acoustic wave generator, a piezoelectric transducer, or an interdigitated transducer (IDT).

The flowing of the mixture relative to a SAW generator can be performed in any appropriate manner, such as gravity flow, an active pumping flow, or other appropriate flow system, such as those described further below. Moreover, the SAW generator can be positioned relative to a selected channel, such as a micro-fluidic channel to generate a SAW relative to the flow channel. It is understood that a flow channel can have any appropriate volume and/or cross-section area. For example, a flow channel may have a cross-section area of about 0.1 micrometers-squared ($\mu^2$) to about 100 centimeters-squared ($cm^2$), and further including about 0.5 $\mu^2$ to about 4 millimeters squared ($mm^2$).

The SAW generator can be used to focus or move a selected material, such as the RBCs from the selected material obtained in block 22, relative to the wash material in the flow channel to assist in directing the selected component to a selected collection volume. Accordingly, the selected sample can be separated in block 28 and the selected sample can be collected in block 30. The separation of the selected sample from the wash material in block 28 can include focusing of the selected sample, including RBCs, in a method similar to that disclosed in U.S. Patent Application Publication No. 2009/0066936 to Huang et al., published Mar. 12, 2009; U.S. Patent Application Publication No. 2010/0139377 to Huang et al., published Jun. 10, 2010; and U.S. Patent Application Publication No. 2012/0196314 to Nawaz et al., published Aug. 2, 2012, incorporated herein by reference. As discussed therein, a SAW generator can be used to direct a flow, such as focus the flow, of a selected component. Also, sheer flows can be used to direct a flow in a selected flow channel. The selected component can be selected based on various features including mass, cell wall elasticity, cell wall density, volume, etc. The collection of the selected sample can be performed in a similar manner. Accordingly, the selected sample can be separated and collected using the SAW generator and/or flow directing systems including those disclosed above.

The wash material can also be optionally collected in block 32. The collection of the wash material may generally include allowing the wash material to flow into a waste container or other disposal system rather than being collected for a specific procedure at a later time. Thus, the reusable collection of the wash material is not required.

After the collection of the selected component, a procedure can be performed with the selected sample in block 40. The selected procedure can be any appropriate procedure, such as infusion of the washed RBCs to a patient, such as a human patient, an animal patient, or the like. The procedure, for example, can be infusion during a medical procedure, such as a surgical procedure, to assist in maintaining an appropriate blood pressure within a patient, or other appropriate procedure. The washed RBCs can also be used in emergency situations to assist in replacing lost blood from a patient. The method can then end in block 42, such as the end of a procedure being performed on a patient.

The collection of a selected sample from the wash material can include the collection of a volume of RBCs that can be used to effectively treat a patient at a selected time. For example, the RBCs can be washed with a wash material and collected in block 30 to apply or be supplied to a patient in an appropriate volume. The procedures can include an infusion and/or transfusion during a surgical procedure and/or an emergency procedure. For example, the collection of the RBCs in block 30 can be at a volume of about 1 milliliters (ml)/minute (min.) to about 100 ml/min., and further including about 1 ml/min. to about 10 ml/min.

Figure 2:
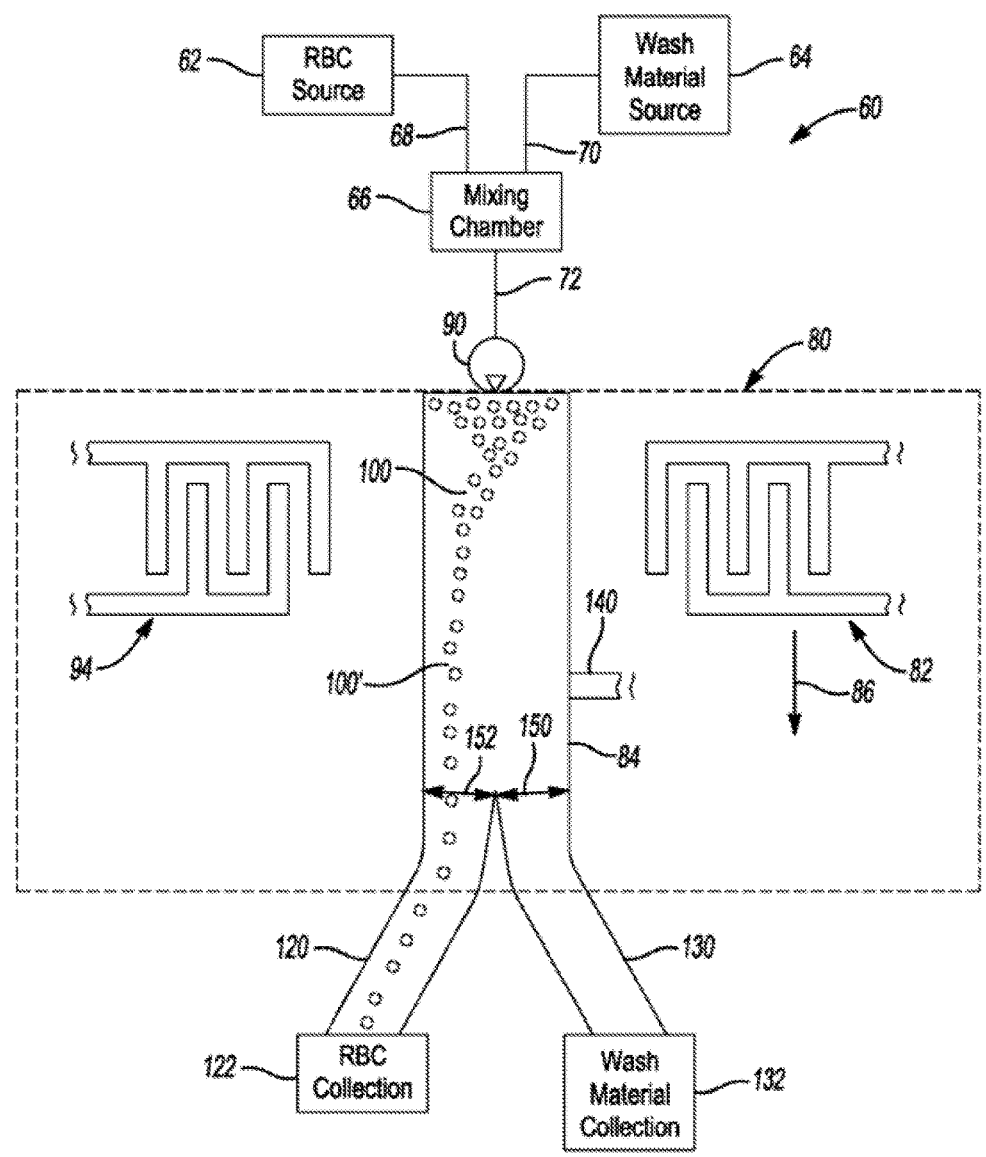
FIG. 2 is a schematic illustration of a separation system.
Figure 3:
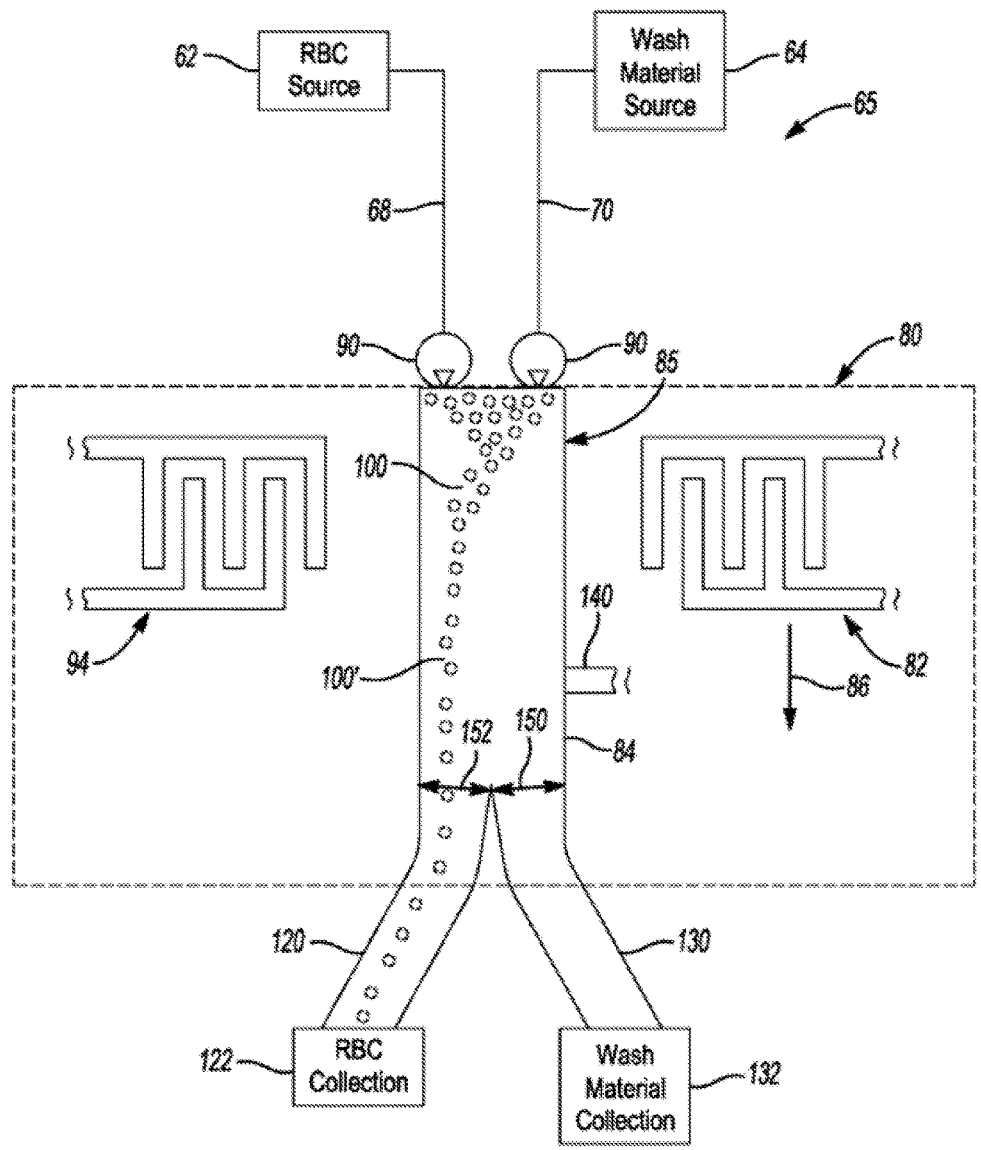
FIG. 3 is a schematic illustration of a second separation system.

According to various embodiments, at least the obtaining sample from block 22, mixing the sample from block 24, flowing the sample passed the SAW generator in block 26, separating and collecting the sample in blocks 28 and 30 of FIG. 1, can be performed with an apparatus 60 illustrated in FIG. 2 or a second apparatus 65 illustrated in FIG. 3. Initially, as schematically illustrated in FIG. 2, the system 60 may include a source of RBCs 62 and a source of wash material 64. The two sources 62, 64 can provide the respective materials, RBCs and wash material, to an external mixing chamber 66. The RBC source 62 can transfer RBCs to the external mixing chamber 66 through a first conduit 68 and the wash material can be passed through a second conduit 70 to the mixing chamber 66. It is understood, however, that a bulk transfer of the RBCs from the RBC source 62 and wash material from the wash materials source 64 can be provided to the mixing chamber 66.

The external mixing chamber 66 can mix the RBCs and the wash material in the process carried out in block 24 of the method 18 discussed above. The mixing can be any appropriate mixing, including those discussed above, such as an agitation or a physical stir bar. Once the mixture of the RBCs in the wash material has occurred for an appropriate time in selected environment controls within the external mixing chamber 66, the mixture can be passed out of or delivered from the mixing chamber through a third conduit 72 to a separating system 80 including a SAW generator 82, such as an acoustic wave generator, a piezoelectric transducer, or an IDT.

The conduit 72 can provide a mixed fluid to a flow conduit 84 and allows a flow of the mixture from the external mixing chamber 66 generally in the direction of arrow 86. In addition, a pump 90 can be used to assist in directing flow or powering flow generally in the direction of arrow 86 through the flow conduit 84. Additionally, it is understood, that at least one second SAW generator 94 can be provided, such as opposed to the first SAW generator 82.

As schematically illustrated in FIG. 3, the second apparatus 65 is similar to the apparatus 60 of FIG. 2. However, the second apparatus 65 lacks the external mixing chamber 66 and the third conduit 72. In the second apparatus 65, the source of RBCs 62 and the source of wash material 64 provide the respective materials, RBCs and wash material, to an internal mixing section 85 of the flow conduit 84, where the RBCs and wash material are mixed together. The RBC source 62 can transfer RBCs to the internal mixing section 85 through the first conduit 68 and the wash material can be passed through the second conduit 70 to the mixing section 85.

The conduits 68, 70 can provide RBCs and wash material to the mixing section 85 of the flow conduit 84 to generate a mixture and allows a flow of the mixture from the sources of RBCs and wash material 62, 64 generally in the direction of arrow 86. In addition, two pumps 90 can be used to assist in directing flow or powering flow generally in the direction of arrow 86 through the flow conduit 84. Additionally, it is understood, that at least one second SAW generator 94 can be provided, such as opposed to the first SAW generator 82.

With reference to both FIG. 2 and FIG. 3, the SAW generators 82, 94 can generate standing waves, such as standing surface acoustic waves (SSAW) comprising pressure nodes, within the flow channel 84. The SSAW can assist in moving, directing, focusing, and separating the RBCs, illustrated as RBC particles 100 within the conduit 84. The RBC particles 100 can be moved into a focused area or region and in a focused path 100' within at least a selected portion of the flow conduit 84 based upon the delivery of the SSAW. In other words, the RBCs have different characteristics from the wash solution that allow the standing acoustic waves to efficiently separate out the RBCs. These characteristics include cell membrane or wall structure, cell membrane or wall density, cell membrane or wall elasticity, cell size, and/or mass as compared to the wash solution. The focused region 100' can assist in moving the RBCs to a RBC collection path 120 and further to a RBC collection volume 122 to allow for a collection of the RBCs as discussed in block 30 of the method 18. The wash material can move down a wash material path 130 to a wash material collection volume 132, as optionally provided in block 32 of the method 18. Accordingly, the RBCs can be collected in the RBC collection volume 122 and used for a procedure, such as any appropriate procedure performed, including those disclosed or discussed above in block 40 in the method 18.

It is further understood the flow of the RBCs in the focused region 100' can be assisted with a directional or directing flow, such as a focusing flow. For example, a focusing flow inlet 140 can assist in directing and focusing the focus flow of the RBCs 100' towards the RBC collection 122.

The RBCs collected in the collection volume 122 can therefore, be washed with the wash material from the wash material source in block 64 and separated from the wash material in the separation system 80. The separation system 80 can include the SAW generators 82 and 94, or any other appropriate number of SAW generators. Additionally, the directing flow inlet 140 can be provided in the appropriate area and multiple directing flow inlets can be used in further separating the RBCs from the mixing chamber 66, such as pumped-in through the conduit 72.

In addition to the SAW generators 82 and 94 and the directing inlet 140, the separation and collection of the RBCs from the flow conduit 84 can be assisted by exit port sizes with the respective exit paths 120 and 130. For example, a least restricted flow path for the wash material can assist in allowing the wash material to flow along the wash material collection path 130. Accordingly, an exit size 150 of the wash material collection path can be larger than exit size 152 of the RBC collection path 120. For example, the exit size of the wash material collection path 150 can be 10% larger to about 2000% larger than an exit port size 152 of the RBC collection path 120. The wash material may selectively pass through the least restrictive path to the wash collection volume 132.

The type of flow through the flow channel 84 can be selected based upon various flow parameters, including flow speed, flow volume, size of the exit ports 150, 152, and other factors. Accordingly, it is understood that flow through the flow channel 84 can be turbulent flow, laminar flow, or change flow types at different regions within the flow channel 84. The flow types may assist in generating the focused flow area 100' of the RBCs to assist in separation and purity of the selected component, including the RBCs, in the RBC collection volume 122. Generally, the RBC collection volume can include about 50% to about 99%, and further include about 55% to about 85% of the total volume of RBCs that enter the flow channel 84 from the mixing chamber 66 through the conduit 72. Accordingly, the RBC collection volume 122 can include a majority or high volume of the total RBCs initially provided into the separation system 80 to be collected.

Figure 4:
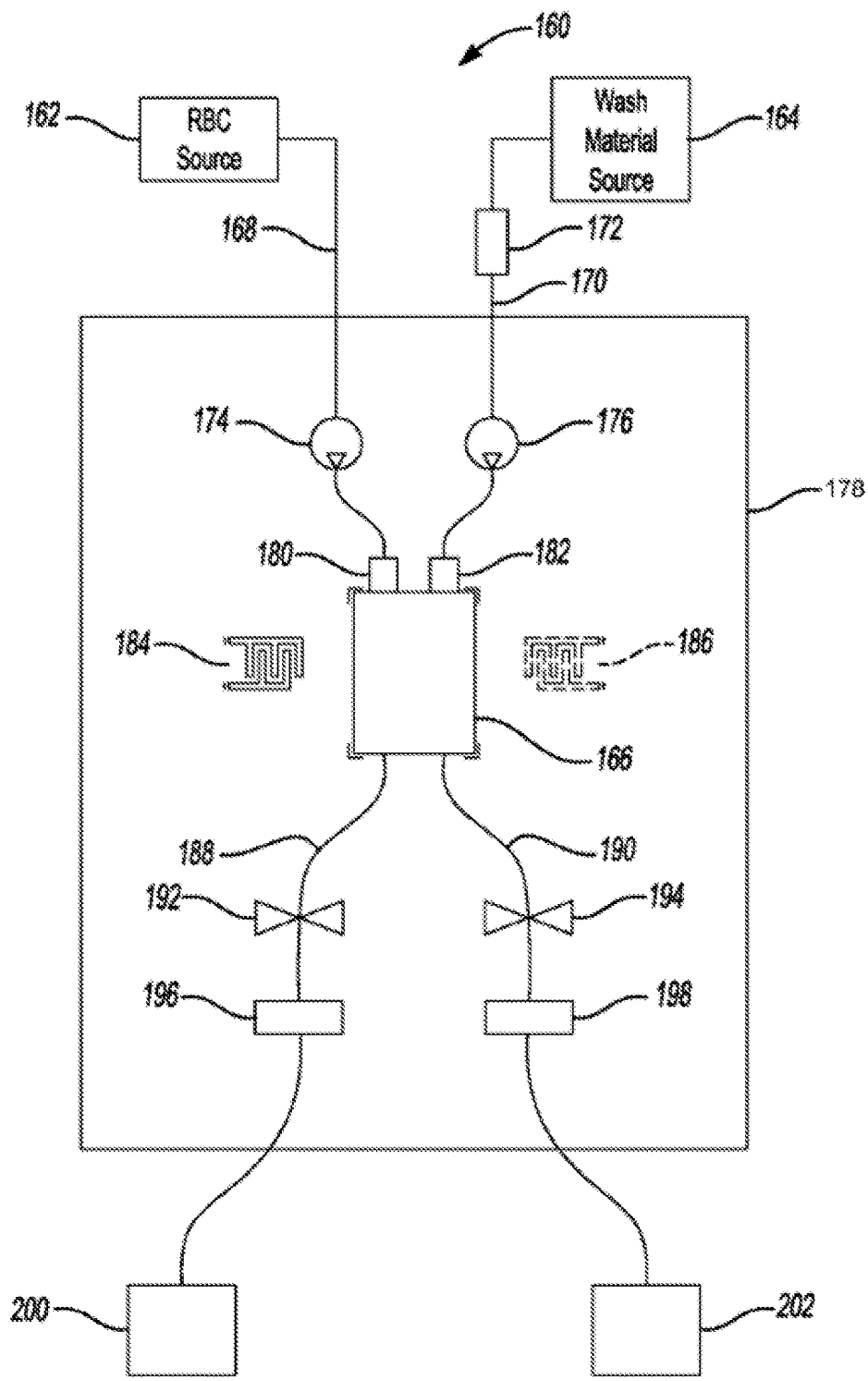
FIG. 4 is a schematic illustration of a third separation system.

Referring to FIG. 4, another system 160 can perform at least the obtaining sample from block 22, mixing the sample from block 24, flowing the sample passed the SAW generator in block 26, and separating and collecting the sample in blocks 28 and 30 of FIG. 1. The system includes a source of RBCs 162 and a source of a wash material 164. The source of a wash material 164 can include any wash material described above with reference to FIG. 1. The two sources 162, 164 can provide the respective materials, RBCs and wash material, to a separation chip 166. The RBC source 162 can transfer RBCs to the separation chip 166 through a first conduit 168 and the wash material can be passed through a second conduit 170 to the separation chip 166. In various embodiments, the second conduit 170 includes a filter 172, which comprises a plurality of pores that sterilizes the wash material and prevents any particulate matter from entering the separation chip 166. The pores can have a diameter of from about 0.1 µm to about 10 µm. In one embodiment, the pore size is about 0.2 µm.

The system 160 also includes a first pump 174 and a second pump 176 to assist in directing flow or powering flow through the first conduit 168 and the second conduit 170, respectively. The first and second pumps 174, 176 can be external units, or the first and second pumps 174, 176 can be permanently or removeably coupled to a base unit 178. For example, the pumps 174, 176 can be peristaltic pumps, rotor-operated pumps, pressure infusors (bag squeezers) or combinations thereof, all further discussed herein. In some embodiments, the pumps 174, 176 provide a steady flow rate, which is devoid of substantial pulses. As used herein, a steady flow rate is a flow rate that has a pulse equal to or less than a desired deviation of about 20%. In various embodiments, a pump with a steady flow rate has a pulse deviation of less than about 15%, less than about 10%, less than about 5%, or less than about 1% of a chosen flow rate. For example, a chosen flow rate of 1000 µL/s that deviates by 100 µL/s has a deviation or pulse of 10%.

In other embodiments, the first pump 174 and the second pump 176 direct flow through the first conduit 168 and the second conduit 170 through a first pulse dampener or flow restrictor 180 and a second pulse dampener or flow restrictor 182, respectively. As used herein, the term "pulse dampener" is also referred to as a "pulse suppressor" or a "baffle." As described further below, the pulse dampeners and/or flow restrictors 180, 182 each comprise an inlet, an internal chamber, and an outlet. In some embodiments, the outlets have diameters that are smaller than the inlets. Accordingly, each internal chamber acts as an air trap, which helps provide a steady flow rate relative to a flow rate provided by the pumps 174, 176 without the pulse suppressors and/or flow restrictors 180, 182. In one embodiment, the pulse suppressors and/or flow restrictors 180, 182 are coupled to the separation chip 166. In other embodiments, not shown in the figure, materials are directed to the separation chip 166 from the pulse suppressors and/or flow restrictors 180, 182 through additional conduits. The additional conduits can have internal diameters that are equal to or smaller than the internal diameters of the first and second conduits 168, 170.

The separation chip 166 comprises a first flow channel and a second flow channel that converge at a mixing region. The separation chip 166 also includes a separation region, and a first outlet channel and a second outlet channel that are in fluid communication with the separation region. The separation chip 166 is positioned relative to a first acoustic wave generator 184 so that a surface acoustic wave separates washed red blood cells from the washing material at the separation region. The first acoustic wave generator 184 can be any acoustic wave generator commonly used in the art, such as, for example, a piezoelectric transducer (PZT) or interdigitated transducer (IDT). The base unit 178 includes a piezoelectric material at least in a region including the wave generator 184 and the separation chip 166. In some embodiments, mixing and separating occur almost simultaneously as the RBCs are directed through the wash material by the standing acoustic wave.

The separation chip 166 can be made of polymers, plastics or of any medical-grade material. The chip material permits acoustic waves to travel through the separation chip 166 without, or substantially without, distortions or scattering. For example, the chip material can be a material, such as a polymer or plastic, that has an acoustic impedance and attenuation similar to that of water. In other words, acoustic waves travel through the material at a speed similar to the speed that acoustic waves travel through water. In some embodiments, acoustic waves travel through the chip material at a speed slower than the speed that acoustic waves travel through water. In other embodiments, the acoustic waves travel through the chip material at a speed equal to or faster than the speed that acoustic waves travel through water. The chip material allows for acoustic waves to penetrate at least one surface and interact with materials flowing within the chip 166. In some embodiment, the chip 166 has at least one surface that reflects acoustic waves. Additionally, the material of the chip 166 allows the chip 166 to be sterilized by any means commonly used in the art, including by heat sterilization, chemical sterilization, or radiation sterilization. Moreover, the material of the chip 166 should have a nominal surface energy to promote flow of the RBCs or wash material through the flow channels, mixing and separation regions, and outlet channels. Accordingly, at least the flow channels, mixing and separation regions, and outlet channels can be coated with a hydrophilic material to promote flow. The separation chip 166 can be manufactured, for example, by 3-D printing or injection molding. In embodiments where the chip 166 is positioned relative to the wave generator 186 on a region of the base unit 178 including a piezoelectric material, a couplant is positioned between the chip 166 and the piezoelectric material to transfer energy from the wave generator 186 to the chip 166. The couplant can be any couplant used in the art that provides a tight bond or seal between the base unit 178 and the chip 166, such as, for example, silicon-based couplants. The couplant can be a sheet, a fluid, an adhesive or a gel that provides an airless bond and does not impede the speed of acoustic waves. Any couplant that provides a tight seal or bond between the base unit 178 and the chip 166 and that does not impede the speed of acoustic waves or does not substantially impede the speed of acoustic waves can be used as a couplant. In some embodiments, the couplant is a silicon-based adhesive, a UV-curing adhesive, a cyanoacrylate adhesive, or an epoxy adhesive that additionally physically attaches the chip 166 to the base unit 178.

In one embodiment, the acoustic wave generator 184 is positioned opposite of an optional second acoustic wave generator 186. The optional second acoustic wave generator 186 can also be a PZT. In this embodiment, the base unit 178 includes a piezoelectric material at least in a region including the wave generator 184, the second wave generator 186, and the separation chip 166. The first and second wave generators 184, 186 generate acoustic waves that interfere with each other, thus generating a standing surface acoustic wave (SSAW). In another embodiment, the separation chip 166 comprises a reflective surface, which reflects an acoustic wave generated by only the first acoustic wave generator 184 back toward the acoustic wave generator 184, thus generating a SSAW. Where a standing acoustic wave is generated by reflecting an acoustic wave back at the acoustic wave generator 184, the optional second acoustic wave generator 186 is not necessary. The use of a reflective surface positioned relative to an acoustic wave generator to generate a standing acoustic wave is described in U.S. Pat. No. 7,837,040 to Ward et al., issued on Nov. 23, 2010, and U.S. Pat. No. 7,846,382 to Strand et al., issued on Dec. 7, 2010, which are both incorporated herein by reference in their entirety. Whereas in some embodiments the acoustic wave generator 184 is coupled to the base unit 178, in other embodiments, the acoustic wave generator 184 is coupled to the separation chip 166 to generate a SAW.

After separation, the washed RBCs flow through the first outlet channel to a third conduit 188 and waste material flows through the second outlet channel to a fourth conduit 190. The third conduit 188 is positioned through a first valve 192 and the fourth conduit 190 is positioned through a second valve 194. The first and second valves 192, 194 can be any type of valve commonly used in the art, such as, for example, pinch valves. The first and second valves 192, 194 are used to help establish optimal flow rates throughout the system 160. Accordingly, flow can be manipulated to establish a steady flow rate by establishing a flow rate at the pumps 174, 176, by altering outlet diameters of the pulse suppressors 180, 182, and by opening or closing the valves 192, 194. The valves 192 can be permanently or removeably coupled to the base unit 178, or they can be stand-alone valves that are positioned external to the base unit 178.

The system 160 also comprises a first sensor 196 and a second sensor 198. The third and fourth conduits 188, 190 are positioned over the first and second sensors 196, 198, respectively. The sensors 196, 198 sense various properties of the washed RBCs or waste material, which a user can note in order to monitor a washing process. In one embodiment, the sensors 196, 198 are color sensors that sense the color of a material flowing through the third and fourth conduits 188, 190. For example, the first sensor 196 associated with the third conduit 188 may sense the red color of washed RBCs. When the process is through, and only clear wash material is then flowing over the first sensor 196, the first sensor 196 activates an alarm that notifies a user that the process is over. Alternatively, the second sensor 198 may sense the clear nature of the wash material flowing through the fourth conduit 190. If, for some reason, a threshold level of RBCs is being directed into the fourth conduit 190, the second sensor 198 can sense the color change and activate an alarm to notify a user. In various embodiments, the sensors 196, 198 sense an amount of light absorbed by the material in the third or fourth conduits 188, 190, or an amount of light transmitted through the material in the third or fourth conduits 188, 190.

The system 160 also comprises a first collection container 200 coupled to the third conduit 188 and a second collection container 202 coupled to the fourth conduit 190. The first collection container 200, for example, collects washed RBCs and the second collection container 202, for example, collects waste material.

Figure 6:
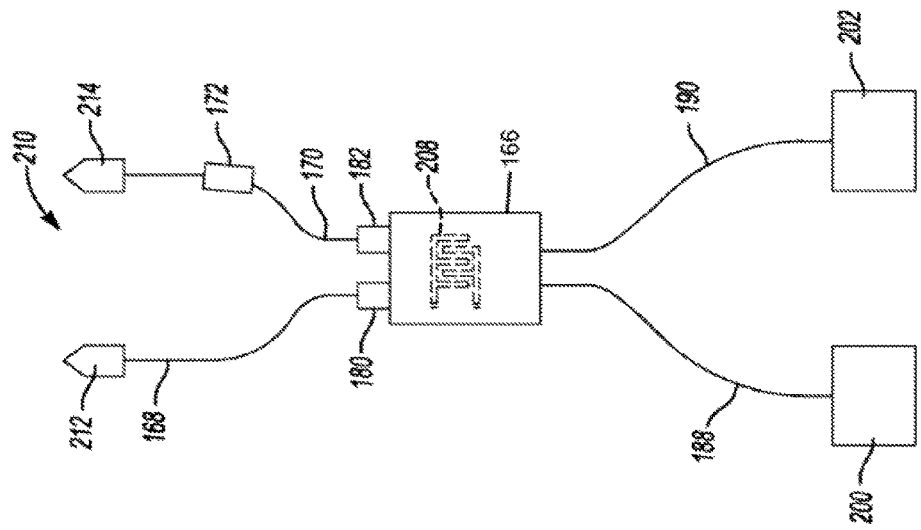
FIG. 6 is a schematic illustration of a disposable set including a separation chip.
Figure 5:
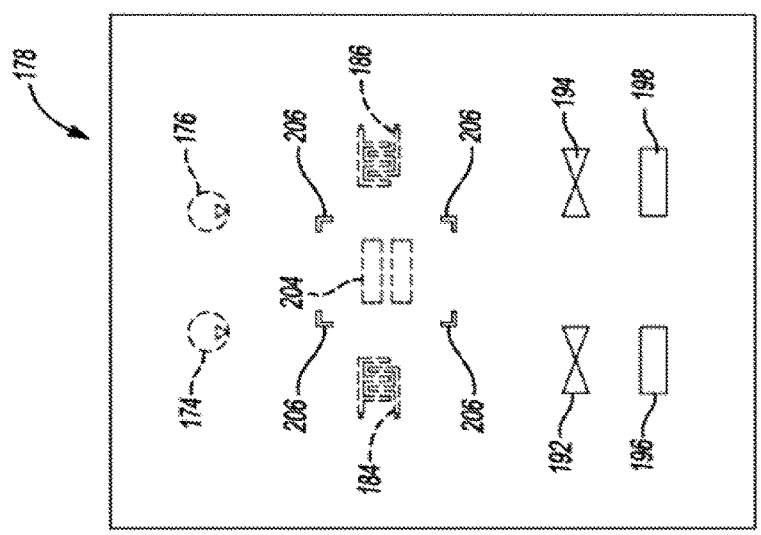
FIG. 5 is a schematic illustration of a base unit for a separation system.

As shown in FIG. 5, multiple components of the system 160 can be coupled to the base unit 178. In one embodiment, the base unit 178 comprises the pinch valves 192, 194, the sensors 196, 198, and optionally the pumps 174, 176. In some embodiments, the pumps 174, 176 are external to the base unit 178. The base unit 178 also comprises either the first wave generator 184 and the second wave generator 186, only the first wave generator 184, or only electrical contacts 204. In embodiments in which the base unit 178 comprises electrical contacts 204, a wave generator 208 (as shown in FIG. 6) is attached to a separation chip. The wave generator 208 is then contacted with the electrical contacts 204 when the separation chip is positioned on the base unit 178. The base unit 178 further comprises a plurality of mounts or cassettes 206 that guide a disposable separation chip in position relative to the wave generator 184 or the electrical contacts 204. Moreover, the mounts or cassettes 206 "snap" the separation chip onto the base unit 178. The base unit can also comprise a plurality of clips that are configured to attached the conduits 168, 170, 188, 190 to the base unit 178 at positions relative to the pumps 174, 176, valves 192, 194, or sensors 196, 198.

As shown in FIG. 6, multiple components of the system 160 can be provided in a preconfigured disposable set 210, which can be positioned on the base unit 178 and simply snapped into place. In one embodiment, there is no need to adjust any component once the disposable set is snapped into position on the base unit 178. The disposable set comprises the separation chip 166, and the first, second, third, and fourth conduits 168, 170, 188, 190. The first conduit has an end that includes a first connecting component 212 that is configured to be coupled to the source of RBCs 162 shown in FIG. 4. The connecting component 212 can be any component commonly used in the art to couple conduit to a source of RBCs. For example, the connecting component 212 can be a component that is welded to the source of RBCs 162 or it can be spike, which is inserted into a port on the source of RBCs 162. The second conduit has an end that includes a second connecting component 214 that is configured to be coupled to the wash material source 164 shown in FIG. 4. The second connecting component 214, for example, can be a spike that can be inserted into a port on the source of the wash material 164. When the base unit 178 includes electrical contacts 204, the separation chip 166 comprises a wave generator 208 for generating a SAW relative to the separation region of the chip 166. In various embodiments, the disposable set 210 also comprises the first collection container 200 coupled to the third conduit 188, the second collection container 202 coupled to the fourth conduit 190, and the filter 172 coupled to the second conduit 170. In an alternative embodiment, the third conduit 188 and the fourth conduit 190 comprise third and fourth connecting components (not shown) for coupling the conduits to waste containers not included in the disposable set 210. In another embodiment, the disposable set 210 also comprises the first and second pulse suppressors and/or flow restrictors 180, 182 either directly coupled to the separation chip 166 or coupled to the separation chip 166 via additional conduits (not shown). Accordingly, the disposable set 210 includes the separation chip 166 and components selected from the group consisting of the first wave generator 184, the first conduit 168, the first connecting component, 212, the second conduit 170, the second connecting component 214, the filter 172, the first pulse suppressor and/or flow restrictor 180, the second pulse suppressor and/or flow restrictor 182, the third conduit, 188, the fourth conduit 190, the first collection container 200, the second collection container 202, the third connecting component, the fourth connecting component, and combinations thereof, wherein the disposable set is attachable to the base unit 178 shown in FIG. 5.

In various embodiments, the conduits 168, 170, 188, 190 are a fixed size, for example, with an inner diameter of from about ⅛ inch to about ½ inch. The disposable set 210 is sterile, and once it is snapped into the base unit 178, a steady flow rate can be established without adjusting the conduits 168, 170, 188, 190 or other components. When snapped into the mounts 206 of the base unit 178, the separation chip 166 is positioned relative to either the first wave generator 184 or the electrical contact 204 of the base unit 178. When the chip 166 is positioned on a base unit 178 that comprises at least the first wave generator 184, a couplant should be placed between the base unit 178 and the chip 166. Suitable couplants are described above.

Pumps

As described above in regard to FIG. 1, FIG. 2, and FIG. 3, a pump 90 can be used to assist in directing flow from the mixing chamber 66 to the flow conduit 84 or two pumps 90 can be used to assist in directing flow from the source of RBCs 62 and the source of the wash material 64 to the flow conduit 84. As described in FIG. 4, two pumps 174, 176 can be used to direct flow from an RBC source 162 and a wash material source 164 to a separation chip 166. The pump(s) 90, 174, 176 can be any pump commonly used in the art. For example, the pump(s) 90 can be a peristaltic pump, a syringe pump, a rotary pump, or a pressure infusor. In exemplary pressure infusor is an AD1000 air driven automatic pressure infusor with regulators by Mallinckrodt Pharmaceuticals (Dublin, Ireland). In various embodiments, the pump is a rotary pump, wherein flow is established and maintained by a rotating rotor within a pump housing. One such pump has a rotor with a cross section shape that is generally square, but with rounded edges. This pump is described in detail in U.S. Pat. No. 7,674,100 to Hayes-Pankhurst et al., issued Mar. 9, 2010, which is incorporated herein by reference in its entirety. Hereinafter, this pump is referred to as a "Hayes-Pankhurst pump," and the rotor of the Hayes-Pankhurst pump is referred to as a "Hayes-Pankhurst rotor." However, one drawback of the Hayes-Pankhurst pump is that the cross-sectional shape of the rotor results in a pulsed flow.

Figures 7, 8:
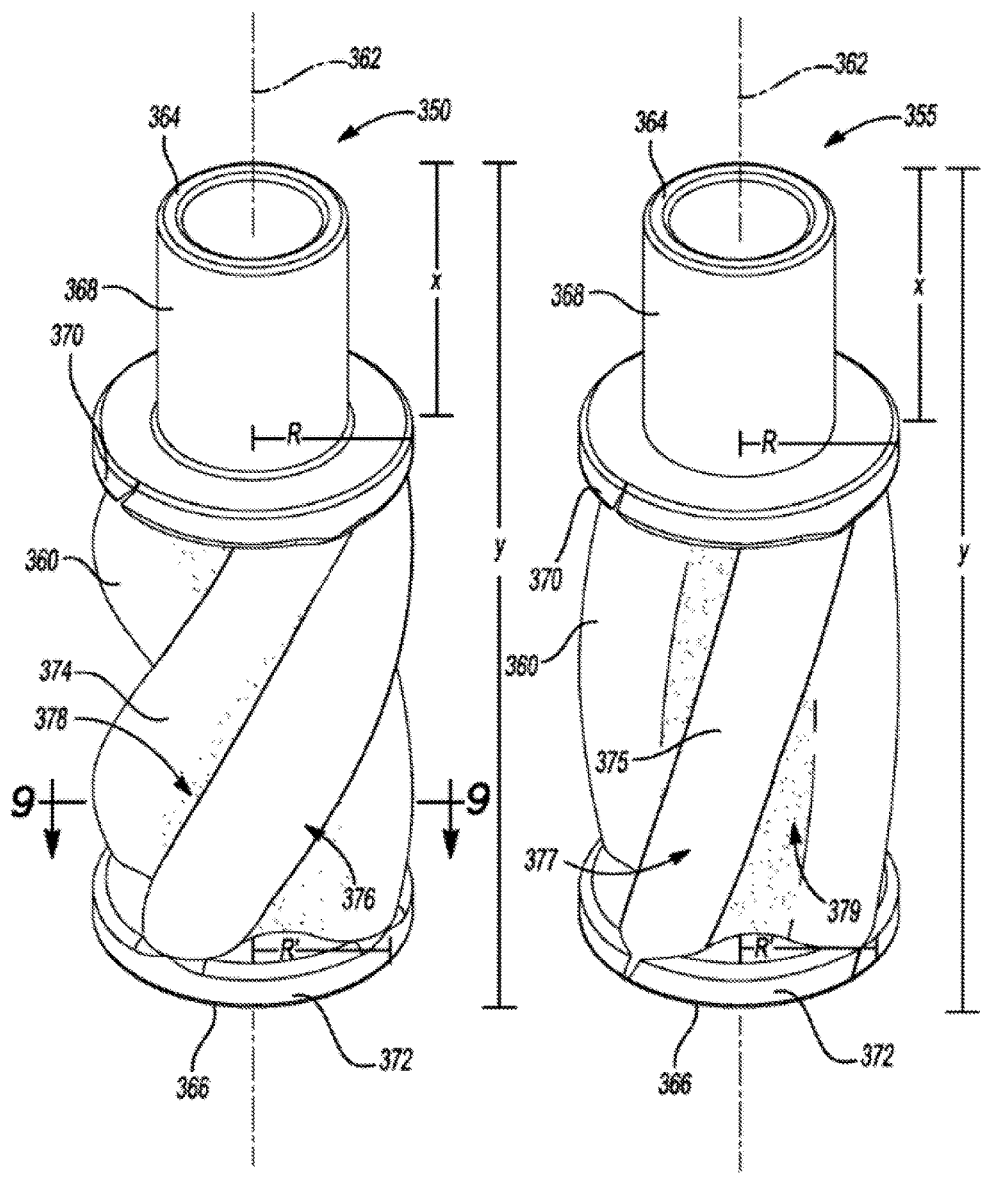
FIG. 7 is a schematic illustration of a first rotor for a rotary pump.
FIG. 8 is a schematic illustration of a second rotor for a rotary pump.

FIGS. 7 and 8 show rotors 350, 355 according to the current technology. The numeric identifiers are the same except for where the rotors 350, 355 differ. The rotor 350 has a body 360 extending along a central longitudinal axis 362 from a first end 364 to a second end 366. The body 360 defines a sleeve 368 that extends from the first end 364 of the body 360 along the central longitudinal axis 362 towards the second end 366 of the body 360. Accordingly, the sleeve 368 has a first end 364 that is the same as the first end 364 of the body 360. The sleeve 368 ends at an annular lip 370 that extends radially from the body 360 about the central longitudinal axis 362. The annular lip 370 has a radius R that extends radially from the central longitudinal axis 362. The annular lip 370 is at a distance X from the first end 364 of the body 360. In various embodiments, the distance X is from about ¹⁄₁₆ to about ¾ of the total length Y of the rotor body 360. The total length Y of the rotor 350 can be from about 0.25 inches to about 2 inches. The sleeve 368 can have any cross-sectional geometry, such as a circle, rectangle, square, triangle, hexagon, or diamond. The sleeve 368 is configured to receive a drive shaft (not shown), which is powered to turn the rotor in a clockwise or counterclockwise direction. The rotor 350 may be formed of stainless steel or as a precision injection molded plastics part formed from a resin. In some embodiments, the rotor 350 is formed of a biocompatible plastic, such as polypropylene.

The second end 366 of the rotor body 360 is configured as a disc 372 with a radius R' that extends radially from the central longitudinal axis 362. In one embodiment, the radius R' of the disc 372 is the same as the radius R of the annular lip 370. The rotor body 360 also defines a plurality of equidistant lobes or ridges 374 that extend from the annular lip 370 and spiral around the central longitudinal axis 362 to the disc 372 at the second end 366 of the rotor body 360. In various embodiments, the lobes can make from a ⅛ turn about the central longitudinal axis 362 to a full turn about the central longitudinal axis 362 per inch. In other embodiments, the lobes 374 make greater than a full turn about the central longitudinal axis 362. As shown in FIG. 7, the lobes 374 make a ½ turn about the central longitudinal axis 362. In other words, the lobes make about a 180° turn about the central longitudinal axis 362. Although it is understood that the rotors according to the current technology can have any number of lobes, such as from 2 to 10 lobes, the rotor 350 shown in has 4 lobes. In FIG. 8, the rotor 355 is similar to the rotor 350 of FIG. 7, but each of the four lobes 375 make a ¼ turn about the central longitudinal axis 362 per inch. In other words, the lobes 375 make about a 90° turn about the central longitudinal axis. Rotor 355 has lobe peaks 377 and valleys 379. In other embodiments, the lobes can make from about a 10° turn per inch to about a 270° turn per inch about the central longitudinal axis. The pumping capacity of the rotors 350, 355 is determined in part by the length of the rotor 350, 355, the size of the lobes 374, 375, and the number of turns the lobes 374, 375 make about the axis 362.

Figure 9:
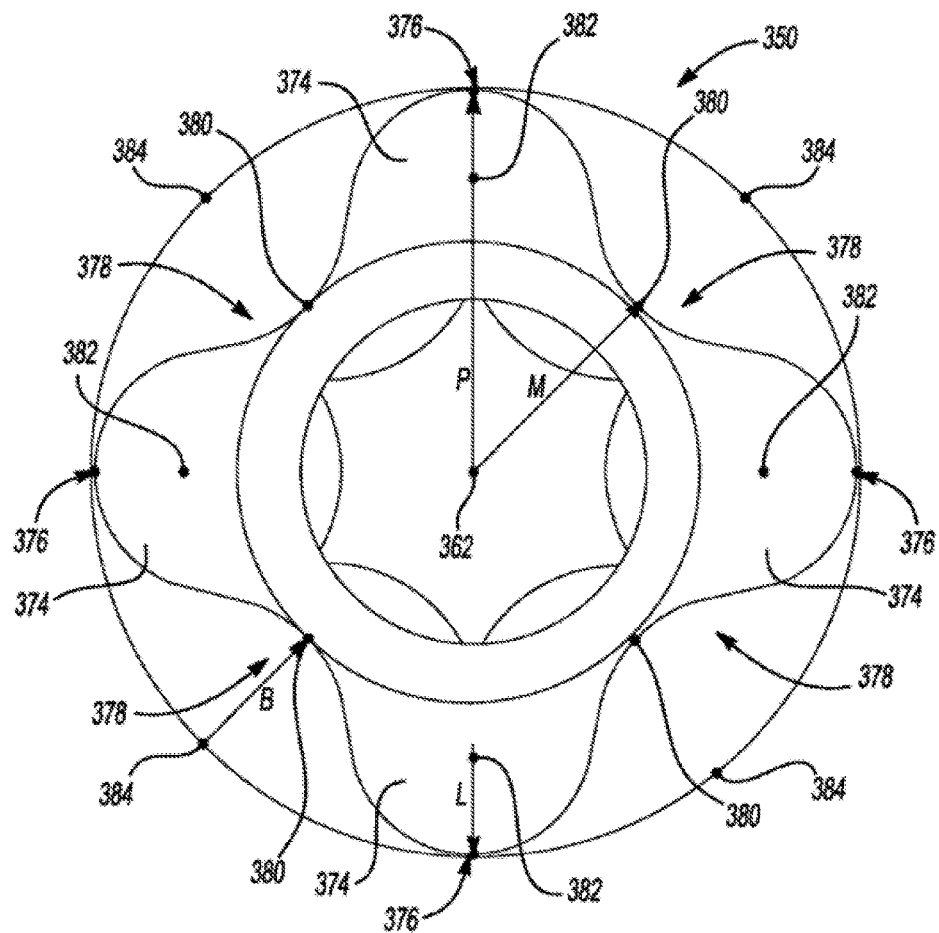
FIG. 9 is a cross-sectional perspective of the first rotor taken along line 9 of FIG. 7.

FIG. 9 is a cross-sectional view of the rotor 350 of FIG. 7 taken along line 6. As shown in the figure, the plurality of lobes 374 have peaks 376 that are a distance P from the central longitudinal axis 362. The plurality of lobes define a plurality of valleys or boluses 378 that separate the lobes 374 from each other. The lobes 374 are separated by a midpoint 380, which is where the valleys 378 are deepest. The midpoints 380 are at a distance M from the central longitudinal axis. The lobes 374 are also defined by a lobe radius L from a point 382 at the center of a lobe 374 to the peak 376 of a lobe 374. Also, the boluses 378 can be defined by a bolus radius B from a point 384 at a distance P from the central longitudinal axis to the midpoint 380 of the bolus 378. The cross section shows a geometric shape, a hexagon, about the longitudinal central axis 362, which is configured to receive a driveshaft (not shown). The driveshaft is powered by a motor and provides a torque to the rotor 350. As described above, the cross sectional geometric shape can be any shape that allows for a torque to be applied to the rotor.

Figure 10:
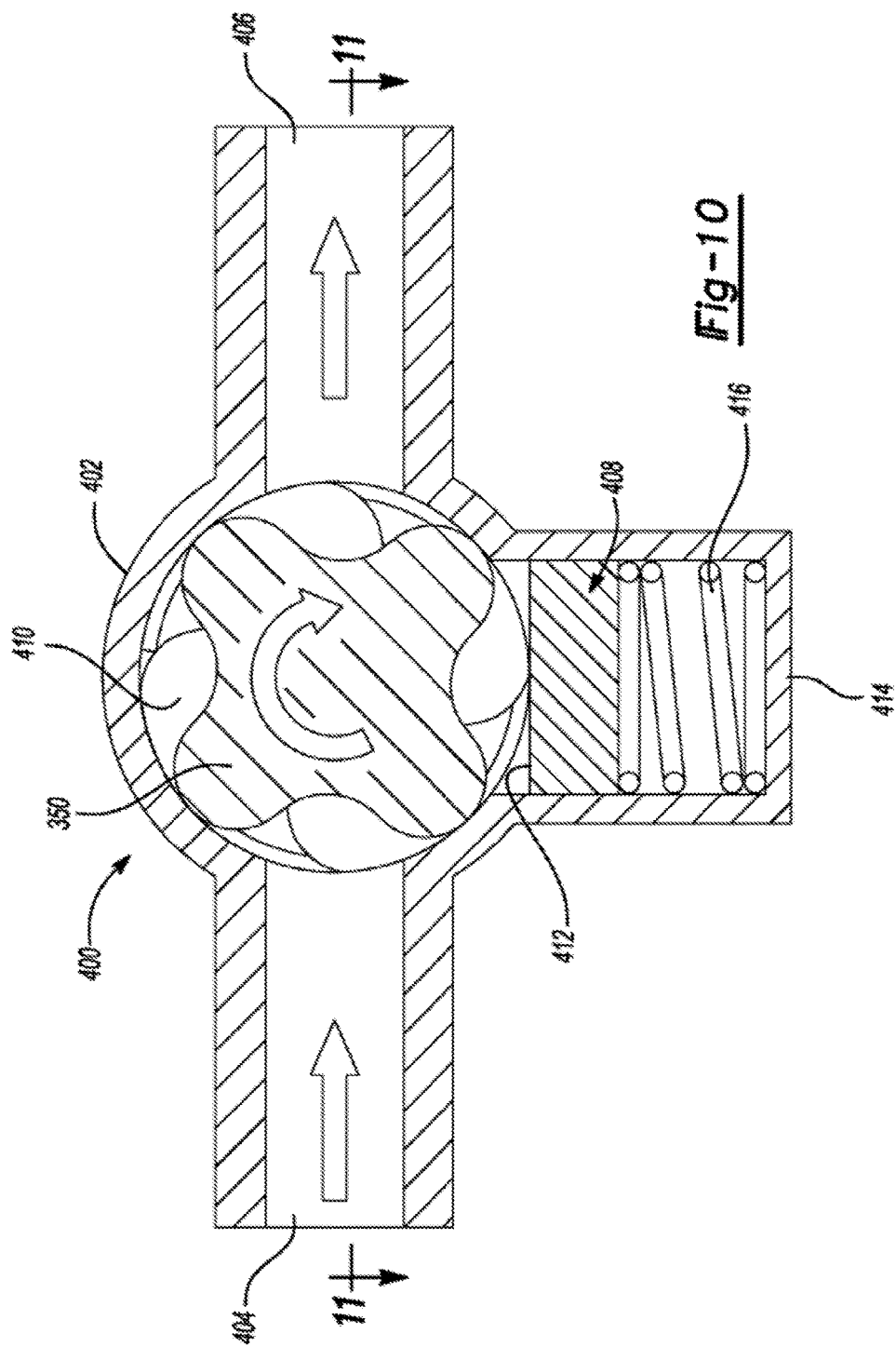
FIG. 10 is cross-sectional view of a pump that shows a rotor positioned within a pump housing in a first perspective.
Figure 11:
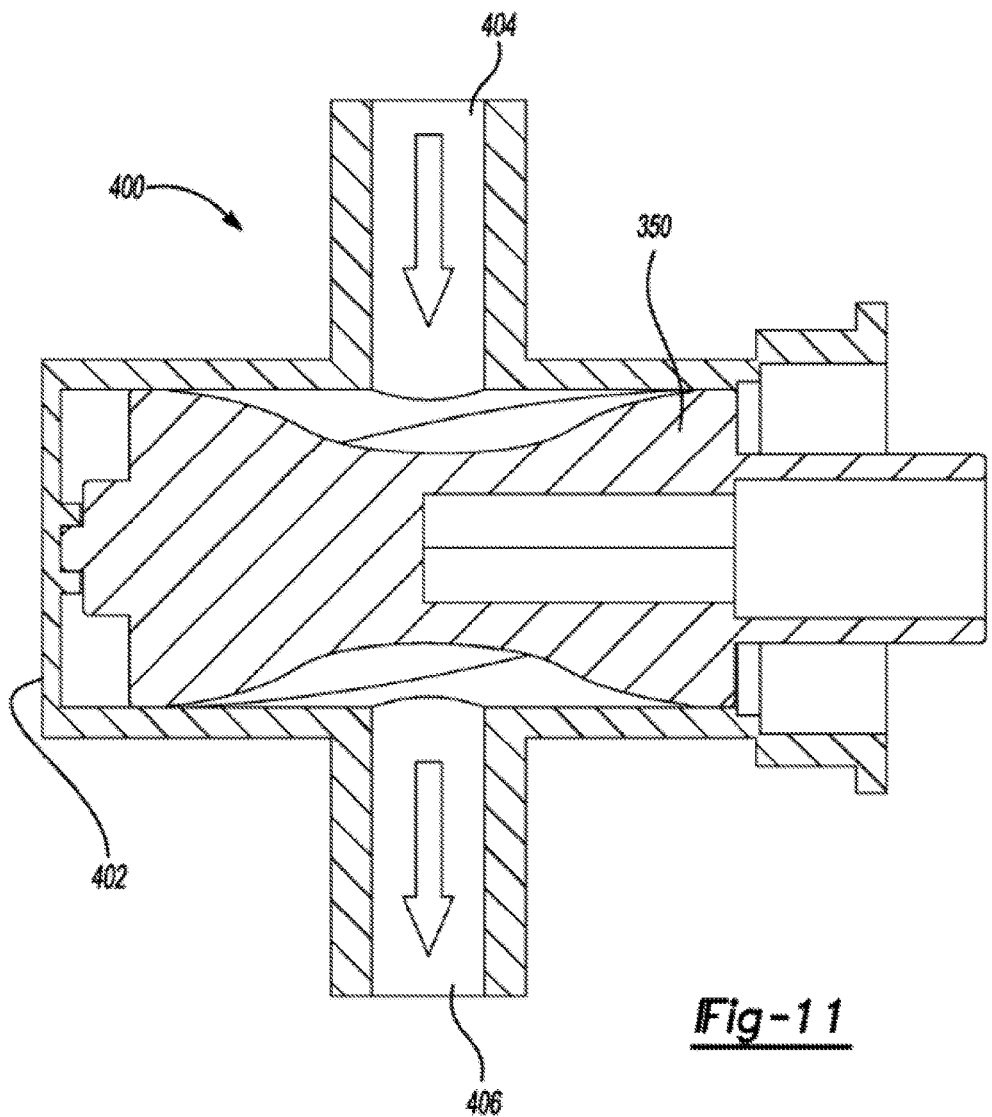
FIG. 11 is a cross-sectional perspective of the pump shown in FIG. 10 taken along line 11 that shows a rotor positioned within a pump housing in a second perspective.

FIGS. 10 and 11 show cross-sectional views a pump 400. The pump 400 has a housing 402, an inlet 404, an outlet 406, and a diaphragm 408 positioned between the inlet 404 and the outlet 406. The housing 402 may be formed by a plastic molding of, for example, polyethylene or polypropylene. The interior of the housing 402 is cylindrical and contains the rotor 350 (shown in FIGS. 7 and 9). Four flow chambers 410 are formed between midpoint 380 of the valleys 378 and the cylindrical interior of the housing 402. When the rotor 350 is rotated in a clockwise direction, forward flow can be established and maintained from the inlet 404 toward the outlet 406. When the rotor 350 is rotated in a counterclockwise direction, backward flow can be established and maintained from the outlet 406 toward the inlet 404. Although FIG. 10 shows four flow chambers 410, the number of flow chambers varies depending on the number of lobes present on the rotor.

The diaphragm 408 is formed by a block of elastomeric material that is compliant, flexible, and resilient. In some embodiments, the diaphragm 408 is formed of polyethylene or polypropylene. The diaphragm 408 has a rotor engaging surface 412, which prevents fluid from flowing in a wrong direction, for example, toward the inlet 404 during forward flow, or toward the outlet during backward flow. The diaphragm is compressed between the rotor 350 and a plate 414 so that constant pressure can be applied to the rotor 350. In some embodiments, an optional spring 416 is positioned between the diaphragm 408 and the plate 414, to further compress the diaphragm 408 against the rotor 350. In some embodiments, the pump 400 has a housing 402, an inlet 404, and an outlet 406, but no diaphragm or spring or plate. In these embodiments, the cylindrical interior of the housing 402 provides a sufficient amount of pressure on the fluid and rotor 350.

During operation, the inlet 404 is coupled to a conduit, such as one of the conduits 68, 70, 72 described in FIGS. 2 and 3, and the outlet is coupled to another conduit, such as the flow conduit 84. Upon rotation of the rotor 350 in a clockwise direction, fluid flows from the conduit, through the inlet 404, and into a chamber 410. As the rotor 350 continues to rotate, the spiral nature of the chambers 410 carries the fluid toward and through the outlet 406 as another chamber 410 rotates about the inlet 404. This mechanism allows for a continuous, steady and smooth flow of fluid through the outlet 406 because the amount of fluid entering the valleys 378 at the inlet 404, and thus the chambers 410, is constant at any point in time as the rotor 350 rotates. The pump 400 can pump fluids with a substantially steady flow rate of from about 0.5 μL/s to about 5 mL/s with a variance of only from about 0.1 μL/s (at a flow rate of about 0.5 μL/s) to about 200 μL/s (at a flow rate of about 5 mL/s). In some embodiments, described further below, a baffle (also referred to as a pulse dampener or a pulse suppressor) and or a flow restrictor is coupled to the outlet 406 or to the conduit that is coupled to the outlet 406 to remove pulsation from the fluid and to provide an even smoother flow. The baffle, which is a small pressure accumulator in-line between the pump and the SAW generator, can be a simple expansion chamber that allows fluid to enter a first baffle port and exit a second baffle port that has a slightly smaller diameter than the first baffle port, while maintaining a small amount of trapped air in the chamber, above the fluid. The baffle can be used with or without the diaphragm 408.

Pulse Dampeners and Flow Restrictors

As described above, pulse dampeners or pulse suppressors can be used to provide a steady flow rate relative to a flow rate provided by the pumps. FIG. 12A shows a perspective view of a pulse dampener or suppressor 500. The pulse suppressor 500 corresponds to the pulse dampeners 180, 182 described with reference to FIGS. 4 and 6. FIG. 12B is a cross-sectional perspective of the pulse suppressor 500 along line 12B of FIG. 12A. The pulse suppressor 500 comprises a housing 502 that defines an inlet 504, and outlet 506, and an internal chamber 508. The inlet 504 and the outlet 506 are at opposing sections of the internal chamber 508, and the inlet 504, outlet 506, and internal chamber 508 are in fluid communication with each other. In one embodiment, the internal chamber 508 is cylindrical and is defined by a flat bottom surface 510, a curved cylindrical side surface 512, and a flat circular top surface 514 that opposes the bottom surface 510. The internal chamber 508 can have a volume of from about 0.25 mL to about 50 mL. In various embodiments, the internal chamber 508 has a volume of about 1 mL, about 2 mL, about 3 mL, about 4 mL, about 5 mL, about 6 mL, about 7 mL, about 8 mL, about 9 mL, about 10 mL, about 15 mL, about 20 mL, about 25 mL, about 30 mL, about 35 mL, about 40 mL, about 45 mL or about 50 mL.

The pulse dampener 500 has a flow path that is nonlinear in that fluid enters the inlet 504 and then flows through a curved inlet channel 516 before entering the internal chamber 508 at the bottom surface 510. The curved inlet channel 516 has a curve of from about 45° to about 90°. In one embodiment, the inlet channel 516 has a curve of about 90°. Likewise, fluid exiting the internal chamber 508 flows through a curved outlet channel 518 that originates at the bottom surface 510 of the internal chamber 508 before exiting through the outlet 506. The curved outlet channel 518 has a curve of from about 45° to about 90°. In one embodiment, the outlet channel 518 has a curve of about 90°.

The inlet 504 has an internal diameter D and the outlet 506 has an internal diameter D', wherein D is equal to or greater than D'. The inlet diameter D and outlet diameter D' can independently be from about 1 mm to about 20 mm with the proviso that the D is equal to or greater than D'. Because, in some embodiments, the inlet 504 is larger than the outlet 506, fluid enters the internal chamber 508 at a faster rate than it exits the internal chamber 508, which results in air being trapped in the internal chamber 508 and a buildup of pressure. Even though fluid may be entering the internal chamber 508 at a pulsed rate provided by a pump, the pressure buildup causes the fluid in the chamber 508 to be expelled out the outlet 506 at a steadier flow rate relative to the pulsed flow rate of the fluid entering the chamber 508.

Figure 13A:
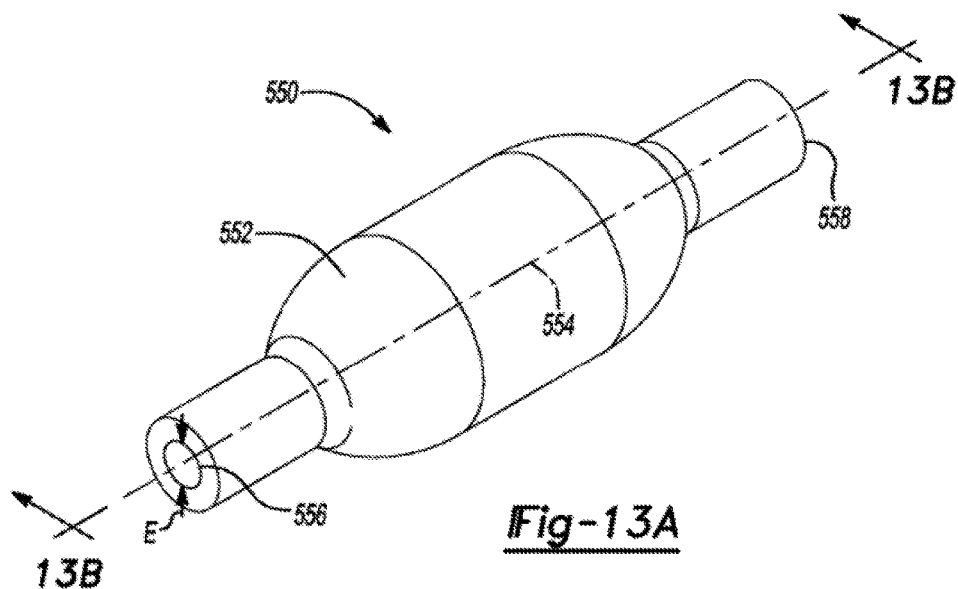
FIG. 13A is a schematic illustration of a flow restrictor.
Figure 13B:
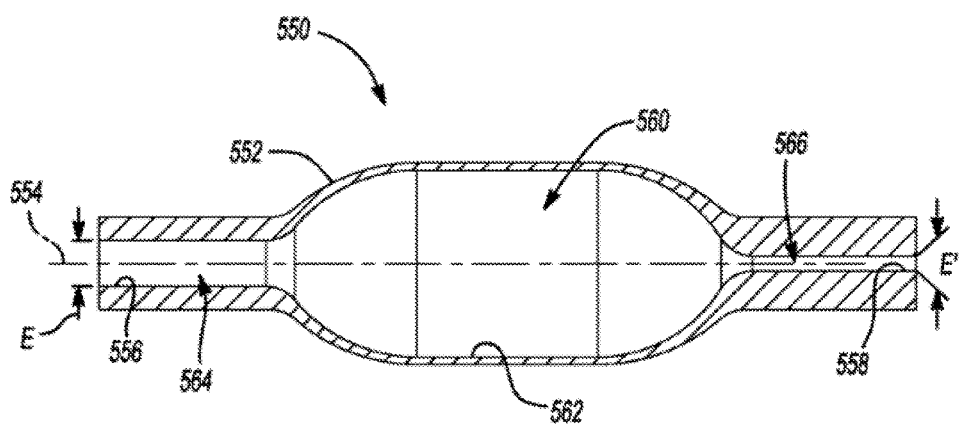
FIG. 13B is a cross-sectional perspective of the flow restrictor taken along line 13B of FIG. 13A.

FIG. 13A shows a perspective view of a flow restrictor 550 according to the present technology. The flow restrictor 550 corresponds to the flow restrictors 180, 182 described with reference to FIGS. 4 and 6. FIG. 13B is a cross-sectional perspective of the flow restrictor 550 along line 13B of FIG. 13A. The flow restrictor 550 comprises a housing 552 that extents around a central axis 554 and defines an inlet 556, and outlet 558, and an internal chamber 560. The inlet 556 and the outlet 58 are at opposing ends of the internal chamber 560, and the inlet 556, outlet 558, and internal chamber 560 are in fluid communication with each other. The internal chamber 560 is substantially cylindrical and is defined by an inner surface 562. The internal chamber 560 can have a volume of from about 0.25 mL to about 50 mL. In various embodiments, the internal chamber 560 has a volume of about 1 mL, about 2 mL, about 3 mL, about 4 mL, about 5 mL, about 6 mL, about 7 mL, about 8 mL, about 9 mL, about 10 mL, about 15 mL, about 20, mL, about 25, mL, about 30 mL, about 35 mL, about 40 mL, about 45 mL or about 50 mL.

The flow restrictor 550 has a linear flow path. Fluid enters the inlet 556 and then flows through a straight inlet channel 564 before entering the internal chamber 560. Likewise, fluid exiting the internal chamber 560 flows through a straight outlet channel 566 before exiting through the outlet 558. The inlet 556, inlet channel 564, internal chamber 560, outlet channel 566, and outlet 558 are all concentric about the axis 554.

The inlet 556 has an internal diameter E and the outlet 558 has an internal diameter E', wherein E is greater than E'. The inlet diameter E and outlet diameter E' can independently be from about 1 mm to about 20 mm with the proviso that the E is greater than E'. Because the inlet 556 is larger than the outlet 558, fluid enters the internal chamber 560 at a faster rate than it exits the internal chamber 560, which results in a buildup of pressure. Even though fluid may be entering the internal chamber 560 at a pulsed rate provided by a pump, the pressure buildup causes the fluid in the chamber 560 to be expelled out the outlet 558 at a steadier flow rate relative to the pulsed flow rate of the fluid entering the chamber 560.

Embodiments of the present technology are further illustrated through the following non-limiting examples.

EXAMPLE 1

Continuous Flow Pumps and Baffles

Pumps according to the present technology were modeled with various rotors. The configuration of the rotors is shown in Table 1, which describes the rotors' names, number of lobes, turns per inch, lob radius, bolus radius, and bolous center (distance from the central longitudinal axis.

TABLE 1

Rotor configurations

| Name | Lobes | Spiral Curve (1/#) | Lobe Radius | Bolus Radius | Bolus Center Distance from Center |
|---|---|---|---|---|---|
| A | 4 | 8 | 0.084 | 0.1 | 0.2602 |
| B | 4 | 8 | 0.09 | 0.098 | 0.2654 |
| C | 4 | 7 | 0.084 | 0.098 | 0.2574 |
| D | 4 | 6 | 0.084 | 0.098 | 0.2574 |
| E | 4 | 5 | 0.084 | 0.098 | 0.2574 |
| F | 4 | 4.75 | 0.084 | 0.098 | 0.2574 |
| G | 4 | 4.5 | 0.084 | 0.098 | 0.2574 |
| H | 4 | 4.25 | 0.084 | 0.098 | 0.2574 |
| I | 4 | 4 | 0.084 | 0.15 | 0.3241 |
| J | 4 | 4 | 0.084 | 0.085 | 0.2382 |
| K | 4 | 4 | 0.1 | 0.098 | 0.2768 |
| L | 4 | 4 | 0.075 | 0.098 | 0.2432 |
| 8T-3L | 3 | 8 | 0.0929 | 0.21 | 0.3500 |
| 8T-4L | 4 | 8 | 0.084 | 0.098 | 0.2574 |
| 8T-5L | 5 | 8 | 0.0929 | 0.009 | 0.1500 |
| 8T-6L | 6 | 8 | 0.0874 | 0.043 | 0.2500 |
| 2T-3L | 3 | 2 | 0.0929 | 0.129 | 0.2500 |
| 2T-4L | 4 | 2 | 0.084 | 0.098 | 0.2574 |
| 2T-5L | 5 | 2 | 0.0929 | 0.009 | 0.1500 |
| 2T-6L | 6 | 2 | 0.0874 | 0.043 | 0.2500 |
| 4T-3L | 3 | 4 | 0.0929 | 0.129 | 0.2500 |
| 4T-4L | 4 | 4 | 0.084 | 0.098 | 0.2574 |
| 4T-5L | 5 | 4 | 0.0929 | 0.009 | 0.1500 |
| 4T-6L | 6 | 4 | 0.0874 | 0.043 | 0.2500 |

The pumps were tested for their ability to deliver a smooth, continuous flow of water. A Hayes-Pankhurst pump and a peristaltic pump were used as controls. The peristaltic pump was a Variable Flow Peristaltic Pump, 4.0-85 mL/min, from Control Company (Friendswood, Tex.). Some of the pumps were used in conjunction with a baffle (pulse suppressor) designed according to the present disclosure. Each pump, in turn, was connected to a fluid circuit consisting of a supply/return tank, a Sensirion SQL-QT500 liquid flow meter, and ¼" tubing with appropriate connectors to allow inserting a "pulse baffle" for some tests. Each pump was adjusted to operate within the range of the flow meter and given time to stabilize before recording the output.

FIG. 9 is a graph that shows how the various pumps performed. The y-axis represents flow rate in µL/s and the x-axis represents time in seconds. By graphing flow rate versus time, flow profiles were achieved. As shown in FIG. 9, the peristaltic pump used without a baffle produced a highly variant flow rate (890 µL/s +/− about 1175 µL/s), which is indicative of pulsed flow. However, when used with a baffle, the peristaltic pump generated a much smoother flow rate of about 710 µL/s +/− about 40 µL/s. The Hayes-Pankhurst pump used without a baffled produced a highly pulsed flow of about 1050 µL/s +/− about 720 µL/s. However, the flow profile only slightly improved when the Hayes-Pankhurst pump was used in conjunction with a baffle (about 800 µL/s +/− about 340 µL/s). In contrast, pumps with rotors 4T-4L and 8T-4L according to the current disclosure, used without a baffle, generated a much smoother flow rate relative to the peristaltic pump without a baffle and the Hayes-Pankhurst pump with and without a baffle. Specifically, the pumps with rotors 4T-4L and 8T-4L produced flow rates of about 1130 µL/s +/− about 90 µL/s and about 935 µL/s +/− about 130 µL/s, respectively. When used with a baffle, the pump with rotor 4T-4L generated a smooth, continues flow rate, comparable to the peristaltic pump used with a baffle. In other words, a substantially steady flow rate of about 1170 µL/s with a variance of about +/− about 55 µL/s was achieved with rotor 4T-4L.

EXAMPLE 2

Pulse Suppressors and Flow Restrictors

A pulse suppressor according to the present technology was manufactured according to FIGS. 12A and 12B. The pulse suppressor has inlet and outlet ports having the same inner diameter and an internal chamber that holds a volume of about 20 mL. The internal chamber has a side surface with a height of about 1 inch. Both the inlet and the outlet accommodate tubing with a ⅛ inch inner diameter.

A flow restrictor according to the present technology was manufactured according to FIGS. 13A and 13B. The flow restrictor has an inlet with a ⅛ inch inner diameter and an outlet with an inner diameter of about 1 mm. The flow restrictor has an internal chamber that holds a volume of about 3 mL.

Flow was initiated and maintained through tubing with a ⅛ inch inner diameter by a Watson-Marlow 114 peristaltic pump (Watson-Marlow Pumps Group, Wilmington, Mass.). Alternatively, flow could be established and maintained by a pressure infusor, as described above. The pulse suppressor and flow restrictor were tested individually and in combination with the peristaltic pump set at a flow rate of 600 µL/s. A SLQ-QT500 flow sensor (Sensirion AG, Switzerland) was positioned in line downstream of the pulse suppressor or flow restrictor to measure the flow rates resulting from each configuration. A control flow profile was obtained by flowing water through the flow sensor without the use of a pulse suppressor or flow restrictor.

Figure 15:
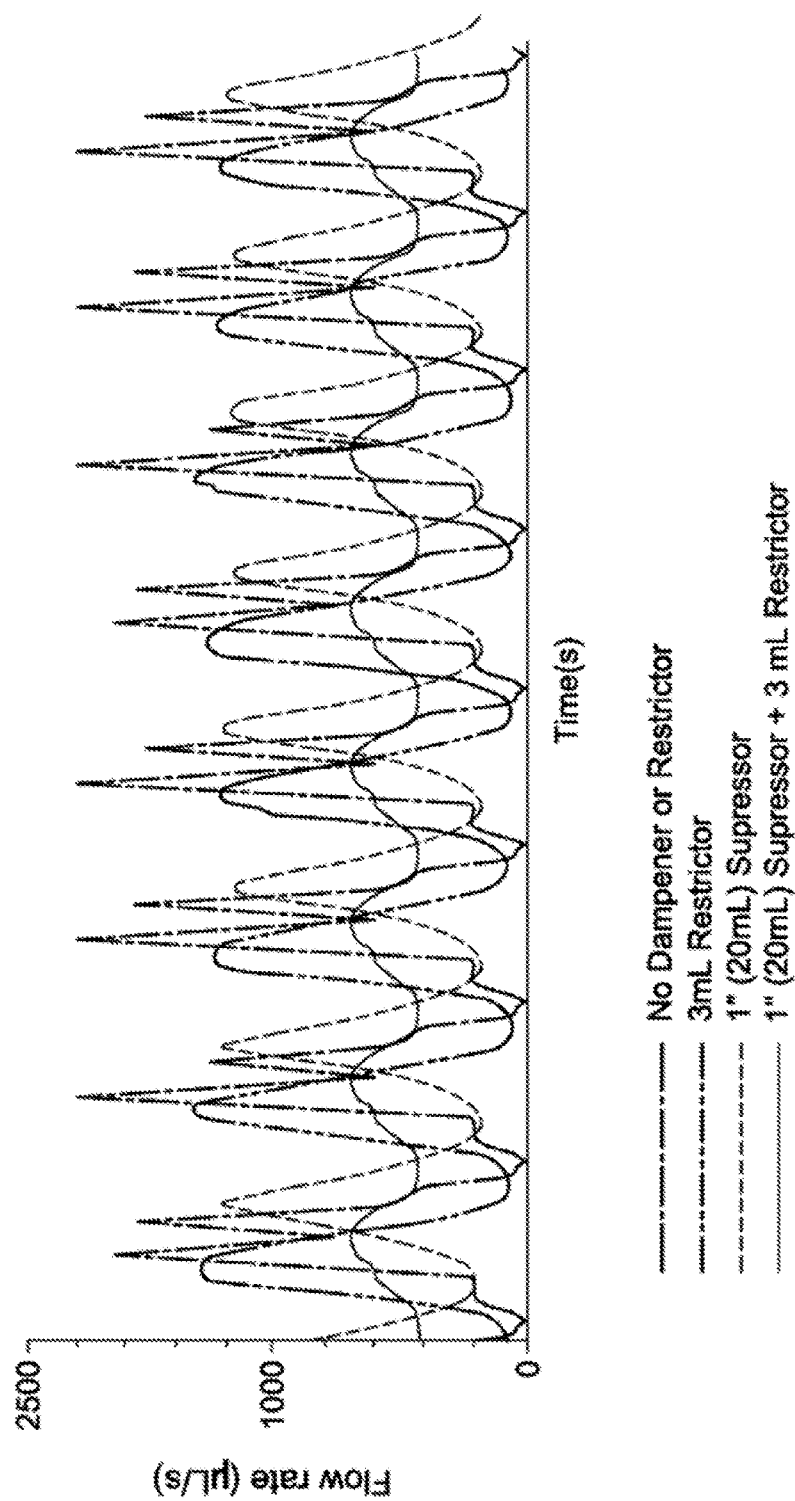
FIG. 15 is a graph that shows flow rates obtained with the use of a pulse suppressor or flow restrictor.

The graph shown in FIG. 15 provides flow profiles obtained according to the various configurations. As shown in FIG. 15, the control configuration (no dampener or restrictor) resulted in a highly variant flow rate, indicative of pulsed flow. However, the flow profile was improved by the addition of the flow restrictor. The configuration including the 20 mL suppressor improved the flow file to a greater extent than the 3 mL flow restrictor. Finally, a configuration including the 20 mL suppressor and the 3 mL flow restrictor, positioned downstream of the suppressor, resulted in the steadiest flow rate obtained.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A system for separating a component from a wash material, the system comprising:
   a base unit comprising mounts and either a wave generator or electrical contacts and components selected from the group consisting of first and second pumps, first and second valves, first and second sensors, a plurality of clips and combinations thereof; and
   a disposable set comprising a separation chip coupled to a first pulse suppressor and a second pulse suppressor, a first conduit coupled to the first pulse suppressor at a first end of the first conduit, and a second conduit coupled to the second pulse suppressor at a first end of the second conduit, and a third and fourth conduit coupled to the separation chip at a first end of the third conduit and at a first end of the fourth conduit,
   wherein the separation chip includes a wave generator when the base unit comprises electrical contacts, and
   wherein the separation chip of the disposable set snaps into the mounts of the base unit.

2. The system according to claim 1, wherein the disposable set further comprises a filter coupled to the second conduit, a connecting component positioned at a second end of the first conduit and a connecting component positioned at a second end of the second conduit.

3. The system according to claim 1, wherein the disposable set further comprises a first waste container coupled to a second end of the third conduit and a second waste container coupled to a second end of the fourth conduit.

4. The system according to claim 1, wherein the base unit comprises an electrical contact, and the separation chip includes a wave generator on one surface, wherein the wave generator contacts the electrical contact when the chip snaps into the mounts of the base unit.

5. The system according to claim 1, wherein the base unit comprises a first wave generator and the disposable set comprises a chip with a reflective surface.

6. The system according to claim 1, wherein the base unit comprises a first wave generator and a second wave generator, wherein the first and second wave generators are positioned to generate a standing surface acoustic wave relative to the chip when the chip is snapped into the mounts of the base unit.

7. The system according to claim 1, wherein the separation chip comprises a first flow channel and a second flow channel that converge at a mixing region, a separation region extending from the mixing region, and first and second outlet channels extending from the separation region.

8. A system for separating a component from a wash material, the system comprising:
   a disposable set comprising a separation chip comprising a first channel, and second channel, the first and second channels converging at a mixing region, a separation region extending from the mixing region, a first outlet channel and a second outlet channel extending from the separation region at an end opposite the mixing region, wherein the disposable set further comprises a first conduit coupled to the separation chip and in fluid communication with the first channel, and a second conduit coupled to the separation chip and in fluid communication with the second channel, and wherein the first and second conduits are coupled to the separation chip through a first pulse dampener and a second pulse dampener, respectively.

9. The system according to claim 8, wherein the first and second pulse dampeners comprise a housing that defines an inlet having an inlet diameter, an outlet having an outlet diameter, and an internal chamber, wherein the inlet, outlet, and internal chamber are in fluid communication with each other, and wherein the outlet diameter is less than the inlet diameter.

10. The system according to claim 9, wherein the pulse dampeners have a flow path that is linear or nonlinear.

11. The system according to claim 8, further comprises a third conduit coupled to the separation chip and in fluid communication with the first outlet channel and a fourth conduit coupled to the separation chip and in fluid communication with the second outlet channel.

12. The system according to claim 8, further comprising:
a base unit comprising mounts for removeably coupling the separation chip to the base unit and either: a first wave generator positioned relative to the separation channel when the separation chip is coupled to the base unit, or an electrical contact.

13. The system according to claim 12, wherein the separation chip comprises a wave generator coupled to one surface and the base unit comprises an electrical contact, wherein the wave generator is in direct contact with the electrical contact when the separation chip is coupled to the base unit.

14. The system according to claim 12, wherein the base unit further comprises at least one component selected from the group consisting of a first pump, a second pump, a first valve, a second valve, a first sensor, and a second sensor, and combinations thereof.

15. A method for separating a component from a mixture comprising:
coupling a separation chip to a base unit, wherein the separation chip comprises a first channel, and second channel, the first and second channels converging at a mixing region, a separation region extending from the mixing region, and a first outlet channel and a second outlet channel extending from the separation region at an end opposite the mixing region, wherein the separation region is positioned relative to an acoustic wave;
coupling a first end of a first conduit to a sample source containing a sample comprising the component and a second end of the first conduit to the separation chip, wherein the first conduit is in fluid communication with the first channel;
coupling a first end of a second conduit to a wash material source containing a wash material and a second end of the second conduit to the separation chip, wherein the second conduit is in fluid communication with the second channel;
flowing the sample and the wash material into the chip, wherein they mix in the mixing region to form the mixture; and
separating the component from the mixture by flowing the mixture through the separation region, wherein the base unit comprises mounts and coupling the separation chip to the base unit comprises snapping the separation chip to the mounts.

16. The method according to claim 15, wherein separation chip comprises a wave generator on a bottom surface, and the base unit further comprises electrical contacts, wherein coupling the separation chip to the base unit further comprises contacting the wave generator to the electrical contacts.

17. The method according to claim 15, wherein the base unit further comprises a first wave generator, and wherein coupling the separation chip to the base unit comprises automatically positioning the separation region relative to the wave generator.

18. The method according to claim 17, wherein the separation chip is positioned adjacent to the wave generator.

19. The method according to claim 18, wherein the base unit further comprises a second wave generator opposite the first wave generator, wherein the separation chip is posited between the first and second wave generators.

20. The method according to claim 18, wherein the separation chip has a reflective surface, wherein the separation region is between the reflective surface and the first wave generator.

21. The method according to claim 15, wherein the sample comprises rejuvenated blood, and the component comprises rejuvenated red blood cells.

22. The method according to claim 15, further comprising collecting the component in a first collection container coupled to the first outlet channel.

23. The method according to claim 22, further comprising collecting the wash material in a second collection container coupled to the second outlet channel.

24. The method according to claim 15, wherein the base unit further comprises at least one of a first valve, a second valve, a first sensor, a second sensor, and combinations thereof, and wherein the method further comprises coupling a first end of a third conduit to the first outlet channel and positioning the third conduit relative to at least one of the first valve and the first sensor; and coupling a first end of a fourth conduit to the second outlet channel and positioning the fourth conduit relative to at least one of the second valve and the second sensor.

25. A method for separating a component from a mixture comprising:
coupling a separation chip to a base unit, wherein the separation chip comprises a first channel, and second channel, the first and second channels converging at a mixing region, a separation region extending from the mixing region, and a first outlet channel and a second outlet channel extending from the separation region at an end opposite the mixing region, wherein the separation region is positioned relative to an acoustic wave;
coupling a first end of a first conduit to a sample source containing a sample comprising the component and a second end of the first conduit to the separation chip, wherein the first conduit is in fluid communication with the first channel;
coupling a first end of a second conduit to a wash material source containing a wash material and a second end of the second conduit to the separation chip, wherein the second conduit is in fluid communication with the second channel;
flowing the sample and the wash material into the chip, wherein they mix in the mixing region to form the mixture; and
separating the component from the mixture by flowing the mixture through the separation region, wherein flowing the sample and flowing the wash material comprise coupling the first conduit to a first peristaltic pump and to a first pulse dampener, and coupling the second conduit to a second peristaltic pump and to a second pulse dampener, wherein the peristaltic pumps and pulse dampeners provide substantially steady flow rates.

26. The method according to claim 25, wherein the sample comprises rejuvenated blood, and the component comprises rejuvenated red blood cells.

27. The method according to claim 25, further comprising collecting the component in a first collection container coupled to the first outlet channel.

28. The method according to claim 27, further comprising collecting the wash material in a second collection container coupled to the second outlet channel.

29. A method for separating a component from a mixture comprising:
- coupling a separation chip to a base unit, wherein the separation chip comprises a first channel, and second channel, the first and second channels converging at a mixing region, a separation region extending from the mixing region, and a first outlet channel and a second outlet channel extending from the separation region at an end opposite the mixing region, wherein the separation region is positioned relative to an acoustic wave;
- coupling a first end of a first conduit to a sample source containing a sample comprising the component and a second end of the first conduit to the separation chip, wherein the first conduit is in fluid communication with the first channel;
- coupling a first end of a second conduit to a wash material source containing a wash material and a second end of the second conduit to the separation chip, wherein the second conduit is in fluid communication with the second channel;
- flowing the sample and the wash material into the chip, wherein they mix in the mixing region to form the mixture;
- separating the component from the mixture by flowing the mixture through the separation region;
- collecting the component in a first collection container coupled to the first outlet channel; and
- collecting the wash material in a second collection container coupled to the second outlet channel.

* * * * *